US009421252B2

(12) United States Patent
Bermudes

(10) Patent No.: US 9,421,252 B2
(45) Date of Patent: *Aug. 23, 2016

(54) LIVE BACTERIAL VACCINES RESISTANT TO CARBON DIOXIDE ($CO_2$), ACIDIC PH AND/OR OSMOLARITY FOR VIRAL INFECTION PROPHYLAXIS OR TREATMENT

(71) Applicant: David Gordon Bermudes, Kenwood, CA (US)

(72) Inventor: David Gordon Bermudes, Kenwood, CA (US)

(73) Assignee: AVIEX TECHNOLOGIES, LLC, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,272

(22) Filed: Feb. 4, 2014

(65) Prior Publication Data

US 2015/0017204 A1   Jan. 15, 2015

Related U.S. Application Data

(62) Division of application No. 12/560,947, filed on Sep. 16, 2009, now Pat. No. 8,647,642.

(60) Provisional application No. 61/098,174, filed on Sep. 18, 2008, provisional application No. 61/165,886, filed on Apr. 1, 2009.

(51) Int. Cl.

| | |
|---|---|
| *A61K 39/00* | (2006.01) |
| *A61K 39/02* | (2006.01) |
| *A61K 39/38* | (2006.01) |
| *A61K 39/145* | (2006.01) |
| *C12N 1/20* | (2006.01) |
| *C12N 1/36* | (2006.01) |
| *C12N 9/10* | (2006.01) |
| *C12N 7/00* | (2006.01) |
| *A61K 39/12* | (2006.01) |

(52) U.S. Cl.
CPC .............. *A61K 39/145* (2013.01); *A61K 39/12* (2013.01); *C12N 1/20* (2013.01); *C12N 1/36* (2013.01); *C12N 7/00* (2013.01); *C12N 9/1025* (2013.01); *A61K 2039/522* (2013.01); *A61K 2039/523* (2013.01); *C12N 2760/16034* (2013.01); *C12N 2760/16134* (2013.01)

(58) Field of Classification Search
USPC .......... 424/258.1, 184.1, 200.1, 234.1, 278.1; 514/2.4, 2.8
See application file for complete search history.

(56) References Cited

U.S. PATENT DOCUMENTS

| | | |
|---|---|---|
| 6,248,329 B1 | 6/2001 | Chandrashekar et al. |
| 6,447,784 B1 | 9/2002 | Bermudes et al. |
| 7,056,700 B2 | 6/2006 | Galen |

OTHER PUBLICATIONS

Pentose phosphate pathway from Wikipedia, the free encyclopedia last visited Apr. 27, 2015.*
Rietschel et al Pyrogenicity and Immunogenicity of Lipid A Complexed with Bovine Serum Albumin or Human Serum Albumin Infection and Immunity, Aug. 1973, p. 173-177.*
Low et al., Nat Biotechnol. Jan. 1999;17(1):37-41.Lipid A mutant *Salmonella* with suppressed virulence and TNFalpha Induction retain tumor-targeting in vivo.
Yuhua et al., Oral cytokine gene therapy against murine tumor using attenuated *Salmonella typhimurium* International Journal of Cancer vol. 94, Issue 3, pp. 438-443, Nov. 1, 2001.
Weiss et al., Transfer of eukaryotic expression plasmids to mammalian host cells by bacterial carriers Current Opinion in Biotechnology vol. 12, Issue 5, Oct. 1, 2001, pp. 467-472.
Karsten et al., msbB deletion confers acute sensitivity to CO2 in *Salmonella enterica* serovar Typhimurium that can be suppressed by a loss-of-function mutation in zwf. BMC Microbiol. Aug. 18, 2009;9:170.
Murray et al., J Bacteriol. Oct. 2001;183(19):5554-61. Extragenic suppressors of growth defects in msbB *Salmonella*.
Feng et al., Infect Immun. Jan. 1996;64(1):363-5.P55, an immunogenic but nonprotective 55-kilodalton Borrelia burgdorferi protein in murine Lyme disease.
Hoffman et al., Amino Acids vol. 37, No. 3, 509-521,Tumor-targeting amino acid auxotrophic *Salmonella typhimurium*.
Ku et al.,Attenuated *Salmonella* and Shigella as Carriers for DNA Vaccines Jan. 2003, vol. 11, No. 8-10 , pp. 481-488.
Lundberg et al Infect Immun. Jan. 1999;67(1):436-8.Glucose 6-phosphate dehydrogenase is required for *Salmonella typhimurium* virulence and resistance to reactive oxygen and nitrogen intermediates.
Murray et al Extragenic Suppressors of Growth Defects inmsbB *Salmonella* J. Bacteriol. Oct. 2001 vol. 183 No. 19 5554-5561.

* cited by examiner

*Primary Examiner* — Maria Leavitt
(74) *Attorney, Agent, or Firm* — Steven M. Hoffberg, Esq.; Ostrolenk Faber LLP

(57) ABSTRACT

Gram-negative bacterial mutants resistant stress conditions, including $CO_2$, acid pH, and high osmolarity are provided, having reduced TNF-α induction having a msbB mutation, that are rendered stress-resistant by a mutation in the zwf gene. A method for prophylaxis or treatment of a virally induced disease in a subject comprising administering to said subject attenuated stress-resistant gram-negative bacterial mutants, is also provided, along with Methods for prophylaxis or treatment of a virally induced disease in a subject comprise administering to said subject one or more stress-resistant gram-negative bacterial mutants as vectors for the delivery of one or more therapeutic molecules. The methods provide efficient delivery of therapeutic molecules by stress-resistant gram-negative bacterial mutants engineered to express said therapeutic molecules.

16 Claims, 9 Drawing Sheets

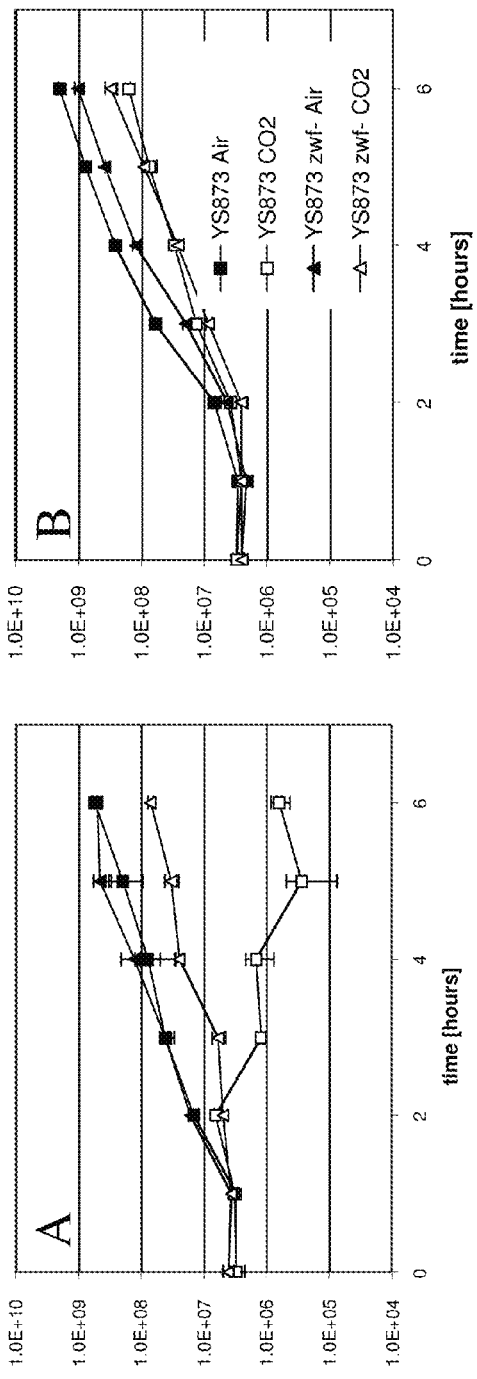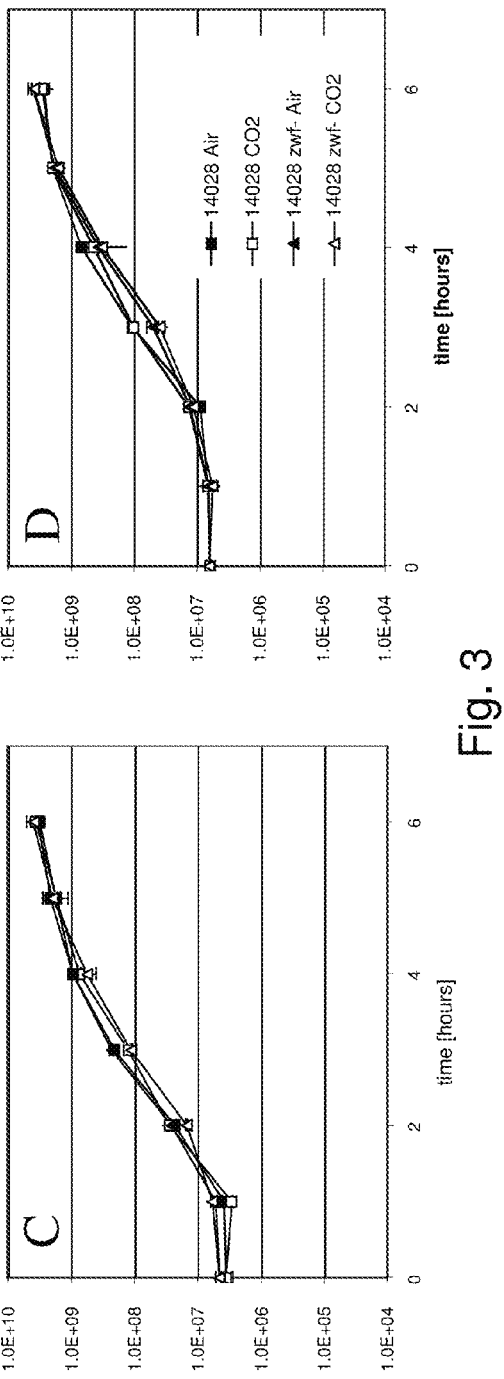
Fig. 3

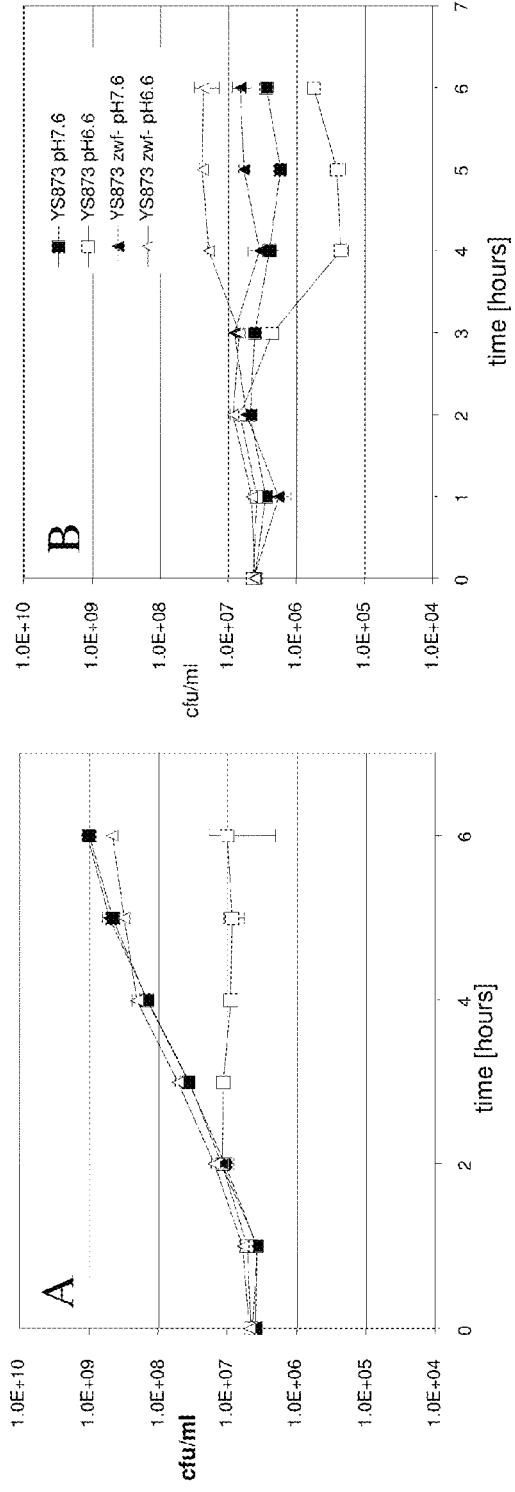
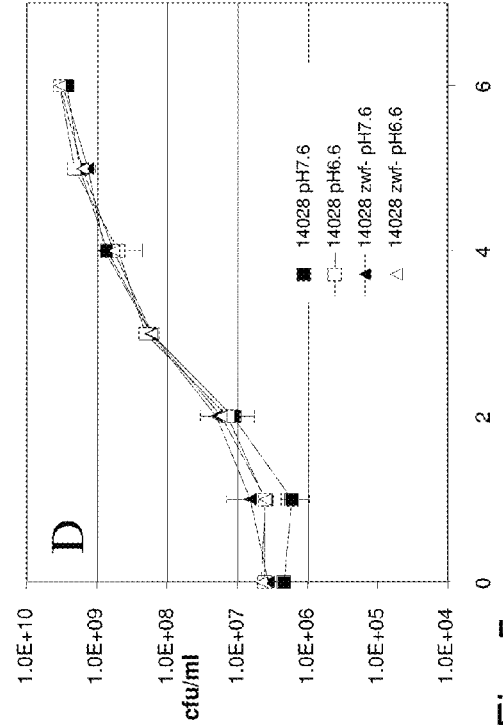
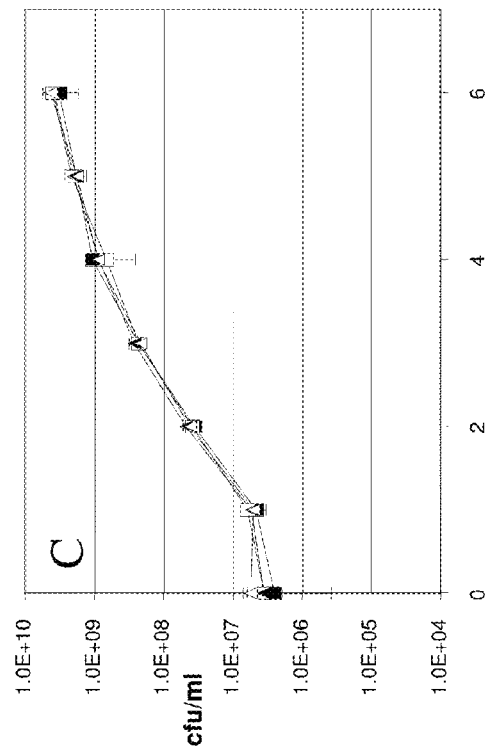
Fig. 5

Fig. 6A  β-gal release in low pH and Air
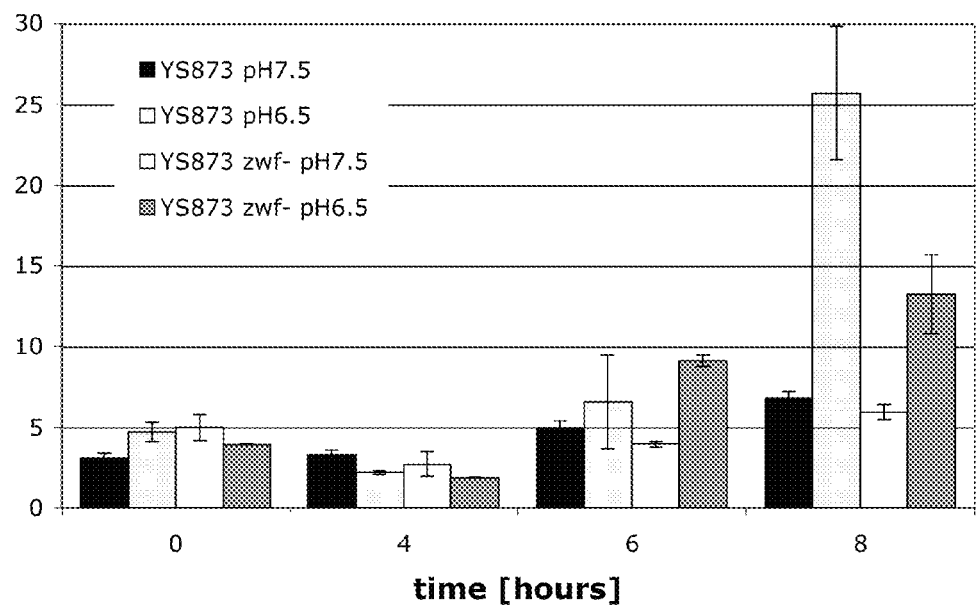
Fig. 6B  β-gal release in low pH and $CO_2$
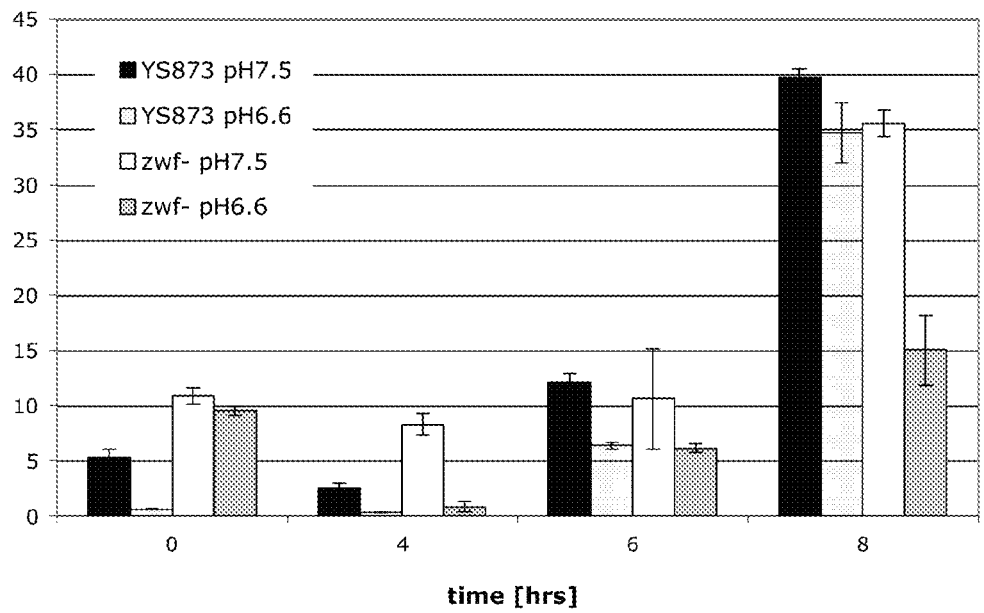

SEQUENCE LISTING

```
<160> NUMBER OF SEQ ID NOS: 6

<210> SEQ ID NO 1
<211> LENGTH: 39
<212> TYPE: DNA
<213> ORGANISM: Salmonella typhimurium

<400> SEQUENCE: 1
gtgtgagctc gtggcttcgc gcgccagcgg cgttccagc                    39

<210> SEQ ID NO 2
<211> LENGTH: 65
<212> TYPE: DNA
<213> ORGANISM: Salmonella typhimurium

<400> SEQUENCE: 2
gtgtgcatgc gggggccat ataggccggg gatttaaatg tcattctcct tagttaatct    60
cctgg                                                          65

<210> SEQ ID NO 3
<211> LENGTH: 57
<212> TYPE: DNA
<213> ORGANISM: Salmonella typhimurium

<400> SEQUENCE: 3
gtgtgcatgc ggggttaatt aaggggggcgg ccgcatttgc cactcactct taggtgg      57

<210> SEQ ID NO 4
<211> LENGTH: 36
<212> TYPE: DNA
<213> ORGANISM: Salmonella typhimurium

<400> SEQUENCE: 4
gtgtgtcgac cctcgcgcag cggcgcatcc ggatgc                         36

<210> SEQ ID NO 5
<211> LENGTH: 20
```

```
<212> TYPE: DNA
<213> ORGANISM: Salmonella typhimurium

<400> SEQUENCE: 5
atattactcc tggcgactgc                                               20

<210> SEQ ID NO 6
<211> LENGTH: 20
<212> TYPE: DNA
<213> ORGANISM: Salmonella typhimurium

<400> SEQUENCE: 6
cgacaatacg ctgtgttacg                                               20
```

LIVE BACTERIAL VACCINES RESISTANT TO CARBON DIOXIDE ($CO_2$), ACIDIC PH AND/OR OSMOLARITY FOR VIRAL INFECTION PROPHYLAXIS OR TREATMENT

CROSS REFERENCE TO RELATED APPLICATIONS

The present application is a Continuation of U.S. patent application Ser. No. 12/560,947, filed Sep. 16, 2009, now U.S. Pat. No. 8,647,642, issued Feb. 11, 2014, which claims benefit of priority from U.S. Provisional Patent Application No. 61/165,886, filed Apr. 1, 2009, and from U.S. Provisional Patent Application No. 61/098,174, filed Sep. 18, 2008, each of which is expressly incorporated herein by reference. This application is also related to U.S. patent application Ser. No. 12/562,532, filed Sep. 18, 2009, now abandoned.

1. FIELD OF THE INVENTION

This invention is generally in the field of live bacterial vaccines for viral infection prophylaxis or treatment.

2. BACKGROUND OF THE INVENTION

Citation or identification of any reference herein, or any section of this application shall not be construed as an admission that such reference is available as prior art to the present application.

There are three types of influenza viruses Influenza A, B, and C. Influenza types A or B viruses cause epidemics of disease almost every winter. In the United States, these winter influenza epidemics can cause illness in 10% to 20% of people and are associated with an average of 36,000 deaths and 114,000 hospitalizations per year. Influenza type C infections cause a mild respiratory illness and are not thought to cause epidemics. Influenza type A viruses are divided into subtypes based on two proteins on the surface of the virus. These proteins are termed hemagglutinin (H) and neuraminidase (N). Influenza A viruses are divided into subtypes based on these two proteins. There are 16 different hemagglutinin subtypes H1, H2, H3, H4, H6, H7, H8, H9 H10 H11 H12, H13, H14, H15 or H16 and 9 different neuraminidase subtypes N1 N2 N3 N4 N5 N6 N7 N8 or N9, all of which have been found among influenza A viruses in wild birds. Wild birds are the primary natural reservoir for all subtypes of influenza A viruses and are thought to be the source of influenza A viruses in all other animals. The current subtypes of influenza A viruses found in people are A(H1N1) and A(H3N2). Influenza B virus is not divided into subtypes.

In 1918, a new highly pathogenic influenza H1N1 pandemic swept the world, killing an estimated 20 and 50 million people. The H1N1 subtype circulated from 1918 until 1957 which then was replaced by viruses of the H2N2 subtype, which continued to circulate until 1968. Since 1968, H3N2 viruses have been found in the population. Because H1N1 viruses returned in 1977, two influenza A viruses are presently co-circulating (Palese and Garcia-Sarstre J. Clin. Invest., July 2002, Volume 110, Number 1, 9-13). The pathogenicity of the initial 1918 H1N1 has not been equaled by any of the latter H1N1, H2N2 or H3N2 subtypes, although infection from some subtypes can be severe and result in death. By molecular reconstruction, the genome of the 1918 flu including the amino acid sequences of the H1 and N1 antigens is now known (Kaiser, Science 310: 28-29, 2005; Tumpey et al., Science 310: 77-81, 2005).

In 1997, 2003, and again in 2004, antigenically-distinct avian H5N1 influenza viruses emerged as pandemic threats to human beings. During each of these outbreaks there was concern that the avian viruses would adapt to become transmissible from human to human. Furthermore, oseltamivir (Tamiflu®) was ineffective in 50% of avian influenza patients in Thailand (Tran et al. N. Engl. J. Med 350: 1179, 2004) and a new mutation in the neuraminidase has been identified which causes resistance to oseltamivir. Sequence analysis of the neuraminidase gene revealed the substitution of tyrosine for histidine at amino acid position 274 (H274Y), associated with high-level resistance to oseltamivir in influenza (N1) viruses (Gubareva et al., Selection of influenza virus mutants in experimentally infected volunteers treated with oseltamivir. J Infect Dis 2001; 183:523-531; de Jong et al., Oseltamivir Resistance during Treatment of Influenza A (H5N1) Infection. N. Engl. J. Med. 353:2667-2672, 2005). Such changes may alter the antigenic nature of the protein and reduce the effectiveness of vaccines not matched to the new variant. Other avian influenza strains of potential danger include H1N1, H7N7 and H9N2.

The optimum way of dealing with a human pandemic virus would be to provide a clinically approved well-matched vaccine (i.e., containing the hemagglutinin and/or neuraminidase antigens of the emerging human pandemic strain), but this cannot easily be achieved on an adequate timescale because of the time consuming method of conventional influenza vaccine production in chicken eggs.

2.1 Live Bacterial Vaccine Vectors

Live attenuated bacterial vaccine vectors offer an important alternative to conventional chicken egg based vaccines. Growth on embryonated hen eggs, followed by purification of viruses from allantoic fluid, is the method by which influenza virus has traditionally been grown for vaccine production. More recently, viruses have been grown on cultured cell lines, which avoids the need to prepare virus strains that are adapted to growth on eggs and avoids contamination of the final vaccine with egg proteins. However, because some of the vaccine virus may be produced in canine tumor cells (e.g., MDCK), there is concern for contamination of the vaccine by cancer causing elements. Moreover, both must undergo a labor intensive and technically challenging purification process, with a total production time of 3 to 6 months. Because of the time factors and scale-up, these vaccines are produced in large, but finite batches. Meeting a world-wide demand requires stockpiling of multiple batches. Therefore, traditionally produced vaccine produced before a pandemic, would likely be generated based upon an avian influenza virus and its antigens more than a year earlier and therefore may not be well matched to an emerging variant and could result in only partial protection. Bacterial vectors self replicate in simple growth media can be produced extremely rapidly by virtue of exponential growth and require minimal purification such as a single centrifugation and resuspension in a pharmaceutically acceptable excipient.

Human studies have shown that antibody titres against hemagglutinin of human influenza virus are correlated with protection (a serum sample hemagglutination-inhibition titre of about 30-40 gives around 50% protection from infection by a homologous virus) (Potter & Oxford (1979) Br Med Bull 35: 69-75). Antibody responses are typically measured by enzyme linked immunosorbent assay (ELISA), immunoblotting, hemagglutination inhibition, by microneutralisation, by single radial immunodiffusion (SRID), and/or by single radial hemolysis (SRH). These assay techniques are well known in the art.

Cellular responses to vaccination may also occur which participate in antiviral immunity. Cells of the immune system are commonly purified from blood, spleen or lymph nodes. Separate cell populations (lymphocytes, granulocytes and monocyte/macrophages and erythrocytes) are usually prepared by density gradient centrifugation through Ficoll-Hypaque or Percoll solutions. Separation is based on the buoyant density of each cell subpopulation at the given osmolality of the solution. Monocytes and neutrophils are also purified by selective adherence. If known subpopulations are to be isolated, for example CD4+ or CD8+ T cells, fluorescence activated cell sorting (FACS) will be employed or magnetic beads coated with specific anti-CD4 or anti-CD8 monoclonal antibody are used. The beads are mixed with peripheral blood leukocytes and only CD4+ or CD8+ cells will bind to the beads, which are then separated out from the non-specific cells with a magnet. Another method depends on killing the undesired populations with specific antibodies and complement. In some cases, a noncytotoxic antibody or other inhibitor can block the activity of a cell subtype. Characterization of cell types and subpopulations can be performed using markers such as specific enzymes, cell surface proteins detected by antibody binding, cell size or morphological identification. Purified or unseparated lymphocytes can be activated for proliferation and DNA synthesis is measured by $^3$H-thymidine incorporation. Other measures of activation such as cytokine production, expression of activation antigens, or increase in cell size are utilized. Activation is accomplished by incubating cells with nonspecific activators such as Concanavalin A, phytohemagglutinin (PHA), phorbol myristic acetate (PMA), an ionophore, an antibody to T cell receptors, or stimulation with specific antigen to which the cells are sensitized.

A key activity of cellular immunity reactions to pathogens such as viruses is the development of T lymphocytes that specifically kill target cells. These activated cells develop during in vivo exposure or by in vitro sensitization. The CTL assay consists of increasing number of sensitized lymphocytes cultured with a fixed number of target cells that have been prelabeled with $^{51}$Cr. To prelabel the target cells, the cells are incubated with the radiolabel. The $^{51}$Cr is taken up and reversibly binds to cytosolic proteins. When these target cells are incubated with sensitized lymphocytes, the target cells are killed and the $^{51}$Cr is released.

Natural killer (NK) cells are an essential defense in the early stage of the immune response to pathogens. NK cells are active in naïve individuals and their numbers can be enhanced in certain circumstances. The NK assay typically uses a $^{51}$Cr-labeled target and is similar to the CTL assay described above.

Specifically activated lymphocytes synthesize and secrete a number of distinctive cytokines. These are quantitated by various ELISA methods. Alternatively, induced cytokines are detected by fluorescence activated flow cytometry (FACS) using fluorescent antibodies that enter permeabilized cells. Activated cells also express new cell surface antigens where the number of cells is quantitated by immunofluorescent microscopy, flow cytometry, or ELISA. Unique cell surface receptors that distinguish cell populations are detected by similar immunochemical methods or by the binding of their specific labeled ligand.

Salmonella bacteria have been recognized as being particularly useful as live "host" vectors for orally administered vaccines because these bacteria are enteric organisms that, when ingested, can infect and persist in the gut (especially the intestines) of humans and animals.

As a variety of Salmonella bacteria are known to be highly virulent to most hosts, e.g., causing typhoid fever or severe diarrhea in humans and other mammals, the virulence of Salmonella bacterial strains toward an individual that is targeted to receive a vaccine composition must be attenuated. Attenuation of virulence of a bacterium is not restricted to the elimination or inhibition of any particular mechanism and may be obtained by mutation of one or more genes in the Salmonella genome (which may include chromosomal and non-chromosomal genetic material). Thus, an "attenuating mutation" may comprise a single site mutation or multiple mutations that may together provide a phenotype of attenuated virulence toward a particular host individual who is to receive a live vaccine composition for avian influenza. In recent years, a variety of bacteria and, particularly, serovars of Salmonella enterica, have been developed that are attenuated for pathogenic virulence in an individual (e.g., humans or other mammals), and thus proposed as useful for developing various live bacterial vaccines (see, e.g., U.S. Pat. Nos. 5,389, 368; 5,468,485; 5,387,744; 5,424,065; Zhang-Barber et al., Vaccine, 17; 2538-2545 (1999); all expressly incorporated herein by reference). In the case of strains of Salmonella, mutations at a number of genetic loci have been shown to attenuate virulence including, but not limited to, the genetic loci phoP, phoQ, cdt, cya, crp, poxA, rpoS, htrA, nuoG, pmi, pabA, pts, damA, purA, purB, purI, zwf, aroA, aroC, gua, cadA, rfc, rjb, rfa, ompR, msbB and combinations thereof.

Bacterial flagella are known to be antigenic and subject to antigenic or phase variation which is believed to help a small portion of the bacteria in escaping the host immune response. The bacterial flagellar antigens are referred to as the H1 and H2 antigens. To avoid confusion with the viral hemagglutinin H antigen, the bacterial flagellar H antigen will be referred to as fH henceforth. Because the Salmonella-based vaccination of a heterologous antigen is dependent upon the bacteria's ability to colonize the gut, which may be reduced do to the initial immune response, the vaccination ability of the second immunization may be diminished due to an immune response to the vector. In Salmonella Hin invertase belongs to the recombinase family, which includes Gin invertase from phage Mu, Cin invertase from phage P1, and resolvases from Tn3 and the transposon (Glasgow et al. 1989, p. 637-659. In D. E. Berg, and M. M. Howe (ed.), Mobile DNA. American Society for Microbiology, Washington, D.C.). Hin promotes the inversion of a chromosomal DNA segment of 996 bp that is flanked by the 26-bp DNA sequences of hixL and hixR (Johnson and Simon. 1985. Cell 41:781-791). Hin-mediated DNA inversion in S. typhimurium leads to the alternative expression of the fH1 and fH2 flagellin genes known as phase variation. Hin (21 kDa) exists in solution as a homodimer and binds to hix sites as a dimer (Glasgow et al. 1989. J. Biol. Chem. 264:10072-10082). In addition to Hin and the two hix sites, a cis-acting DNA sequence (recombinational enhancer) and its binding protein (Fis, 11 KDa) are required for efficient inversion in vitro (Johnson et al. 1986. Cell 46:531-539). Live Salmonella vaccines have not had deletions of the hin gene nor defined fH1 or fH2 antigens, nor have they been constructed such that they lack fH antigens altogether. Accordingly, live Salmonella vaccines have not been constructed to maximize a prime-boost strategy which alternates or eliminates the fH antigen whereby the immune response of the fH antigen of the first immunization (prime) is not specific for the antigen of the second immunization (boost). Therefore, the boost immunization is not diminished by a rapid elimination by the immune system, and is therefore able to persist longer and more effectively present the immunizing antigen.

Introduction of viral genes into bacteria results in genetically engineered microorganisms (GEMs) for which there may be concern regarding containment of the introduced gene in the environment and its ability to reassort. Such genes could in theory provide virulence factors to non-pathogenic or less pathogenic viral strains if allowed to recombine under circumstances were the bacterial vaccine could co-occur at the same time in the same individual as a wild type viral infection. Thus, methods that reduce bacterial recombination and increase bacterial genetic isolation are desirable.

Insertion sequences (IS) are genetic elements that can insert copies of themselves into different sites in a genome. These elements can also mediate various chromosomal rearrangements, including inversions, deletions and fusion of circular DNA segments and alter the expression of adjacent genes. IS200 elements are found in most *Salmonella* species. *S. typhimurium* strain LT2 has six IS200s. *Salmonella typhimurium* strain 14028 has been described to possess an additional IS200 element at centisome 17.7 which is absent in other commonly studied *Salmonella* strains LT2 and SL1344 (Murray et al., 2004 Journal of Bacteriology, 186: 8516-8523). These authors describe a spontaneous hot spot (high frequency) deletion of the Cs 17.7 to Cs 19.9 region. Live *Salmonella* vaccines have not had deletions of IS200 elements which would limit such recombination events.

*Salmonella* strains are known to possess phage and prophage elements. Such phage are often capable of excision and infection of other susceptible strains and are further capable of transferring genes from one strain by a process known as transduction. Live *Salmonella* vaccines have not had deletions in phage elements such as phage recombinases which exist in *Salmonella*, such that the phage are no longer capable of excision and reinfection of other susceptible strains.

*Salmonella* strains are known to be capable of being infected by bacteria phage. Such phage have the potential to carry genetic elements from one *Salmonella* strain to another. Live *Salmonella* vaccines have not comprised mechanisms to limit phage infection such as the implantation and constitutive expression of the P22 phage repressor C2.

Bacterial expression of the viral hemagglutinin genes was first described by Heiland and Gething (Nature 292: 581-582, 1981) and Davis et al., (Proc. Natl. Acad. Sci. USA 78: 5376-5380). These authors suggest that the recombinant protein could be used as a vaccine without regard to the fact that the viral genetic loci are not optimal for bacterial expression. These authors did not suggest the use of live bacterial vectors as vaccine carriers, such as the genetically stabilized and isolated vectors of the present application, nor the use of defined flagellar antigens or no flagellar antigens. Nor did these authors suggest the use of secreted proteins.

Use of secreted proteins in live bacterial vectors has been demonstrated by several authors. Holland et al. (U.S. Pat. No. 5,143,830, expressly incorporated herein by reference) have illustrated the use of fusions with the C-terminal portion of the hemolysin A (hlyA) gene. When co-expressed in the presence of the hemolysin protein secretion channel (hlyBD) and a functional TolC, heterologous fusions are readily secreted from the bacteria. Similarly, Galen et al. (Infection and Immunity 2004 72: 7096-7106) have shown that a heterologous fusions to the ClyA are secreted and immunogenic. Other heterologous protein secretion systems include the use of the autotransporter family. For example, Veiga et al. (2003 Journal of Bacteriology 185: 5585-5590) demonstrated hybrid proteins containing the □-autotransporter domain of the immunoglogulin A (IgA) protease of Nisseria gonorrhea. Fusions to flagellar proteins have also been shown to be immunogenic. The antigen, a peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, expressly incorporated by reference in their entirety herein). Antigenic peptides are selected by various methods, including epitope mapping (Joys and Schodel 1991. Infect. Immune. 59: 3330-3332; Hioe et al., 1990 J. Virol. 64: 6246-6251; Kaverin et al. 2002, J. Gen. Virol. 83: 2497-2505; Hulse et al. 2004, J. Virol. 78: 9954-9964; Kaverin et al. 2007, J. Virol. 81:12911-12917; Cookson and Bevan 1997, J. Immunol. 158: 4310-4319, expressly incorporated by reference in their entirety herein), T-cell epitope determination (Walden, 1996, Current Opinion in Immunology 8: 68-74) and computer programs such as Predict7 (Carmenes et al. 1989 Biochem. Biophys. Res. Comm 159: 687-693) Pepitope (Mayrose et al., 2007. Bioinformatics 23: 3244-3246). Multihybrid FliC insertions of up to 302 amino acids have also been prepared and shown to be antigenic (Tanskanen et al. 2000, Appl. Env. Microbiol. 66: 4152-4156, expressly incorporated by reference in its entirety herein) Modification of the fusion protein by inclusion of flanking cathepsin cleavage sites has been used to facilitate release within the endosomal compartment of antigen presenting cells (Verma et al. 1995 Vaccine 13: 235-244). Trimerization of antigens has been achieved using the T4 fibritin foldon trimerization sequence (Wei et al. 2008, J. Virology 82: 6200-6208, expressly incorporated by reference in its entirety herein).

Bacterial expression of the viral hemagglutinin genes was first described by Heiland and Gething (Nature 292: 581-582, 1981) and Davis et al., (Proc. Natl. Acad. Sci. USA 78: 5376-5380). These authors teach that the antigens may be purified from the bacteria in order to be used as vaccines and did not suggest the use of live attenuated bacterial vectors. Furthermore, the codon usage of the viral genome is not optimal for bacterial expression. Accordingly, a gram-negative bacterium of the enterobacteraceae such as *E. coli* and *Salmonella* will have a different codon usage preference (National Library of Medicine, National Center for Biotechnology Information, GenBank Release 150.0 [Nov. 25, 2005]) and would not be codon optimized. Further, these authors used antibiotic-containing plasmids and did not use stable chromosomal localization. Nor did these authors suggest heterologous fusions in order for the bacteria to secrete the antigens.

Kahn et al. (EP No. 0863211) have suggested use of a live bacterial vaccine with in vivo induction using the *E. coli* nitrite reductase promoter nirB. These authors further suggest that the antigenic determinant may be an antigenic sequence derived from a virus, including influenza virus. However, Khan et al. did not describe a vaccine for avian influenza virus. They did not describe the appropriate antigens for an avian influenza virus, the hemagglutinin and neuraminidase, and did not describe how to genetically match an emerging avian influenza virus. Furthermore, it has become apparent that certain assumptions, and experimental designs described by Khan et al. regarding live avian influenza vaccines would not be genetically isolated or have improved genetic stability in order to provide a live vaccine for avian influenza that would be acceptable for use in humans. For example, Khan et al. state that any of a variety of known strains of bacteria that have an attenuated virulence may be genetically engineered and employed as live bacterial carriers (bacterial vectors) that express antigen polypeptides to elicit an immune response including attenuated strains of *S. typhimurium* and, for use in humans, attenuated strains of *S. typhi* (i.e., *S. enterica* serovar Typhi). In support of such broad teaching, they point to the importance of "non-reverting" mutations, especially deletion mutations which provide the attenuation. However, non-reversion only refers to the particular gene mutated, and not to the genome per se with its variety of IS200, phage and prophage elements capable of a variety of genetic recombinations and/or even transductions to other bacterial strains. Khan et al. did not describe a bacterial strain with improved genetic stability, nor methods to reduce genetic recombination, such as deletion of the IS200 elements. Khan et al. did not describe a bacterial strain with improved genetic stability by deletion of the bacteria phage and prophage elements nor limiting their transducing capacity. Neither did Khan et al. describe methods to minimize bacterial genetic exchange, such as constitutive expression of the P22 C2 phage repressor.

The above comments illustrate that Khan et al. have not provided the field with an effective vaccine against avian influenza. Clearly, needs remain for a genetically isolated and genetically stable, orally administered vaccine against avian influenza which is capable of rapid genetically matching an emerging pathogenic variant.

Bermudes (WO/2008/039408), expressly incorporated herein in its entirety, describes live bacterial vaccines for viral infection prophylaxis or treatment. The bacteria described are live attenuated bacterial strains that express one or more immunogenic polypeptide antigens of a virus. The bacteria useful for the techniques described include *Salmonella, Bordetella, Shigella, Yersenia, Citrobacter, Enterobacter, Klebsiella, Morganella, Proteus, Providencia, Serratia, Plesiomonas*, and *Aeromonas*. Bermudes describes the serovars of *Salmonella. enterica* that may be used as the attenuated bacterium of the live vaccine compositions to include, without limitation, *Salmonella enterica* serovar *Typhimurium* ("*S. typhimurium*"), *Salmonella montevideo, Salmonella enterica* serovar *Typhi* ("*S. typhi*"), *Salmonella enterica* serovar *Paratyphi* B ("*S. paratyphi* 13"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorurn* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anaturn* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *kunzendorf* ("*S. cholerae kunzendorf*"), and *Salmonella enterica* serovar *minnesota* (*S. minnesota*).

Bermudes describes attenuating mutations useful in the *Salmonella* bacterial strains which may include genetic locus selected from the group consisting of phoP, phoQ, edt, cya, crp, poxA, rpoS, htrA, nuoG, pmi, pabA, pts, damA, purA, purB, purI, zwf, purF, aroA, aroB, aroC, aroD, serC, gua, cadA, rfc, rjb, rfa, ompR, msbB and combinations thereof.

Although Bermudes discloses the msbB gene and the zwf gene, it was not recognized that in *Salmonella*, the deletion of the msbB gene confers sensitivity to carbon dioxide ($CO_2$) and that deletion of zwf, a member of the pentose phosphate pathway (Fraenkel, D. G. 1996 Glycolysis, pp 189-198, In *Eschericia coli* and *Salmonella typhimurium*, F. C. Neidehardt (ed), ASM Press, Washington, D.C.), compensates for that deletion and restores resistance to carbon dioxide without losing the low degree of lipid A pyrogenicity (TNF-α induction) conferred by the msbB mutation. Furthermore, it was also not known that the msbB⁻ *Salmonella* are also sensitive to acidic pH and osmolarity, and that the zwf mutation also enhances resistance to acidic pH and osmolarity. Therefore, the prior art does not teach a specific combination of these two mutations in order to obtain $CO_2$ resistant bacteria. Nor would one ordinarily skilled in the arts be motivated to test for $CO_2$ resistance in *Salmonella* deleted in msbB as there is no teaching that describes the occurrence of sensitivity or its importance. As described herein, $CO_2$ and acidic pH-resistant ΔmsbB⁻ bacteria have improved survival under physiological conditions advantageous for penetration into gut mucosal, lymphoidal and dendridic tissues at lower doses, in order to elicit an immune response to viral diseases.

3. SUMMARY OF THE INVENTION

The present invention provides improved live attenuated bacterial strains that express one or more immunogenic polypeptide antigens of a virus, preferably an avian influenza virus, that is effective in raising an immune response in animals, including mammals and birds.

In particular, one aspect of the invention relates to improved live attenuated bacterial strains which may include *Salmonella* vectoring avian influenza antigens that can be administered orally to an individual to elicit an immune response to protect the individual from avian influenza. The invention provides gram-negative bacterial mutants resistant to one or more stress conditions, including, but not limited to, $CO_2$, acid pH, and high osmolarity. In a preferred embodiment, attenuated gram-negative bacterial mutants are provided which are resistant to $CO_2$, acid pH, and/or high osmolarity. In a more preferred embodiment, attenuated gram-negative bacterial msbB⁻ mutants resistant to $CO_2$, acid pH, and high osmolarity are provided. In a more preferred embodiment, attenuated gram-negative bacterial msbB⁻ mutants resistant to $CO_2$, acid pH, and high osmolarity are provided by a mutation in the pentose phosphate pathway. In a specific embodiment, attenuated gram-negative bacterial msbB⁻ mutants resistant to $CO_2$, acid pH, and high osmolarity by deletion or disruption of the zwf gene are provided. However, it should be understood that the scope of the invention is limited by the claims, and not otherwise constricted to particular genotypes or phenotypes.

The preferred bacteria are serovars of *Salmonella*. The preferred *Salmonella* strains of the invention are specifically attenuated by at least one first mutation at genetic locus which, alone or in combination, results in increased sensitivity to $CO_2$, osmolarity and/or acidic pH combined with at least one second mutation that compensates for the increased sensitivity to $CO_2$, osmolarity and acidic pH and restores resistance to $CO_2$, osmolarity and acidic pH. The attenuating mutation resulting in sensitivity to $CO_2$, osmolarity and acidic pH may be those of known lipid biosynthesis genes which exhibit a degree of safety in animals including but not limited to msbB (also known as mlt, waaN, lpxM), firA, kdsA, kdsB, kdtA, lpxA, lpxB, lpxC, lpxD, ssc, pmrA, and htrB. The resistance-conferring gene mutation can be any member of the pentose phosphate pathway, including zwf, pgl, gnd, rpe, rpiA, rpiB, tktA, tktB, talA, talB, especially those genes directly related to gluconate production, including zwf, gnd and pgl, or related gene products that provide gluconate into the pentose pathway including gntT and other transporters for gluconate including but not limited to the homologous gntU, gntP and idnT transporters. The invention also provides stress-resistant gram-negative bacterial mutants engineered to contain and/or express one or more nucleic acid molecules encoding one or more therapeutic molecules.

In one embodiment, stress-resistant gram-negative bacterial mutants are provided which are facultative anaerobes or facultative aerobes. In another embodiment, stress-resistant gram-negative bacterial mutants are provided which are facultative anaerobes or facultative aerobes and that comprise one or more nucleic acid molecules encoding one or more therapeutic molecules. Examples of facultative anaerobes or facultative aerobes include, but are not limited to, *Salmonella typhi, Salmonella choleraesuis*, or *Salmonella enteritidis*.

In a specific embodiment, the present invention provides stress-resistant *Salmonella* mutants. Examples of *Salmonella* sp. which may be used in accordance with the invention include, but are not limited to, *Salmonella typhi, Salmonella choleraesuis*, or *Salmonella enteritidis*. Preferably, the stress-resistant *Salmonella* mutants are attenuated by introducing one or more mutations in one or more genes in the lipopolysaccharide (LPS) biosynthetic pathway, and optionally one or more mutations to auxotrophy for one or more nutrients or metabolites. In a preferred embodiment, attenuated stress-resistant *Salmonella* mutants comprise a genetically modified msbB gene, express an altered lipid A molecule compared to wild-type *Salmonella* sp., and induce TNF-α expression at a level less than that induced by a wild-type *Salmonella* sp. The growth of attenuated stress-resistant *Salmonella* mutants used in accordance with the invention may be sensitive to a chelating agent such as, e.g., Ethylenediaminetetraacetic Acid (EDTA), Ethylene Glycol-bis(β-aminoethyl Ether) N,N,N',N'-Tetraacetic Acid (EGTA), or sodium citrate. For example, a chelating agent may inhibit the growth of attenuated stress-resistant *Salmonella* mutants by about 25%, 50%, 80%, or 99.5% compared to the growth of a wild-type *Salmonella* sp. Preferably, the attenuated stress-resistant *Salmonella* mutants used in accordance with the invention survive in macrophages up to about 1% of the level of survival of a wild-type *Salmonella* sp, preferably up to about 10%, more preferably from about 10% up to about 30%, even more preferably from about 30% up to about 50%, and most preferably up to about 90% or even higher.

In one embodiment, the present invention provides stress-resistant *Salmonella* mutants comprising one or more nucleic acid molecules encoding one or more therapeutic molecules. In a preferred embodiment, the present invention provides attenuated stress-resistant *Salmonella* mutants, wherein the attenuation of the stress-resistant *Salmonella* mutants is due, at least in part, to one or more mutations in the msbB gene. In another preferred embodiment, the present invention provides attenuated stress-resistant *Salmonella* mutants, wherein the attenuated stress-resistant *Salmonella* mutants comprise one or more nucleic acid molecules encoding one or more therapeutic molecules and the attenuation of the stress-resistant *Salmonella* mutants is due, at least in part, to one or more mutations in the msbB gene.

A therapeutic molecule may be, for example, a molecule which directly reduces the cause of a pathological condition, one which enhances host response to a condition or reduces an adverse host response due to the condition, one which reduces the incidence of superinfection or improves host health or immune response, or the like.

In one embodiment, the present invention provides mutant *Salmonella* sp. comprising a genetically modified msbB gene and a mutation characterized by increased growth when grown under $CO_2$ conditions compared to the msbB⁻ mutant *Salmonella* designated YS1646 having ATCC Accession No. 202165 (Low, et. al., 1999, Nature Biotechnology 17: 37-41; Low et al., 2004 Methods Mol. Med. 90: 47-60). In another embodiment, the present invention provides a mutant *Salmonella* sp. comprising a genetically modified msbB gene and a mutation characterized by increased growth when grown in acidified media compared to the msbB⁻ mutant *Salmonella* designated YS1646 having ATCC Accession No. 202165. In yet another embodiment, the present invention provides mutant *Salmonella* sp. comprising a genetically modified msbB gene and a mutation characterized by increased growth in media with high osmolarity compared to the msbB⁻ mutant *Salmonella* designated YS1646 having ATCC Accession No. 202165. In accordance with these embodiments, the mutant *Salmonella* sp. may further comprise one or more genetically modified genes to auxotrophy and/or one or more nucleic acid molecules encoding one or more therapeutic molecules.

In another preferred embodiment, the present invention provides a mutant *Salmonella* sp. comprising a genetically modified msbB gene and a genetically modified zwf gene.

According to various embodiments, the invention provides pharmaceutical compositions comprising pharmaceutically acceptable carriers and one or more stress-resistant gram-negative bacterial mutants. The invention also provides pharmaceutical compositions comprising pharmaceutically acceptable carriers and one or more stress-resistant gram-negative bacterial mutants comprising nucleotide sequences encoding one or more therapeutic molecules. The pharmaceutical compositions of the invention may be used in accordance with the methods of the invention for the prophylaxis or treatment of virally induced disease. Preferably, the stress-resistant gram-negative bacterial mutants are attenuated by introducing one or more mutations in one or more genes in the lipopolysaccharide (LPS) biosynthetic pathway, and optionally one or more mutations to auxotrophy for one or more nutrients or metabolites.

In one embodiment, a pharmaceutical composition comprises a pharmaceutically acceptable carrier and one or more attenuated stress-resistant gram-negative bacterial mutants, wherein said attenuated stress-resistant gram-negative bacterial mutants are facultative anaerobes or facultative aerobes. In another embodiment, a pharmaceutical composition comprises a pharmaceutically acceptable carrier and one or more attenuated stress-resistant gram-negative bacterial mutants, wherein said attenuated stress-resistant gram-negative bacterial mutants are facultative anaerobes or facultative aerobes and comprise one or more nucleic acid molecules encoding one or more therapeutic molecules where the therapeutic molecule is a viral antigen.

In a specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules.

In a preferred embodiment, a pharmaceutical composition comprises a pharmaceutically acceptable carrier and one or more attenuated stress-resistant *Salmonella* mutants. In another preferred embodiment, a pharmaceutical composition comprises a pharmaceutically acceptable carrier and one or more attenuated stress-resistant *Salmonella* mutants, wherein said attenuated stress-resistant *Salmonella* mutants comprise one or more nucleic acid molecules encoding one or more therapeutic molecules.

The present invention encompasses treatment protocols that provide a better therapeutic effect than current existing vaccines. In particular, the present invention provides methods for prophylaxis or treatment of virally induced disease in a subject comprising administering to said subject and one or more stress-resistant gram-negative bacterial mutants, preferably attenuated stress-resistant gram-negative bacterial mutants. The present invention also provides methods for the prophylaxis or treatment of virally induced disease in a subject comprising administering to said subject one or more stress-resistant gram-negative bacterial mutants, preferably attenuated stress-resistant gram-negative bacterial mutants, wherein said stress-resistant gram-negative bacterial mutants comprise one or more nucleic acid molecules encoding one or more therapeutic molecules.

The present invention provides methods for the enhanced delivery of one or more therapeutic molecules in a subject comprising administering to said subject one or more stress-resistant gram-negative bacterial mutants, preferably attenuated stress-resistant gram-negative bacterial mutants, comprising nucleic acid molecules encoding one or more therapeutic molecules. The methods of the present invention permit lower dosages and/or less frequent dosing of stress-resistant gram-negative bacterial mutants (preferably attenuated stress-resistant gram-negative bacterial mutants) to be administered to a subject for prophylaxis or treatment of virally induced disease to achieve a therapeutically effective amount of one or more therapeutic molecules.

In a specific embodiment, the present invention provides a method of prophylaxis or treatment of virally induced disease in a subject, said method comprising administering to said subject an effective amount of a mutant *Salmonella* sp. comprising a genetically modified msbB gene and a mutation characterized by increased growth when grown under $CO_2$ conditions compared to the msbB⁻ mutant *Salmonella* designated YS1646 having ATCC Accession No. 202165. In another embodiment, the present invention provides a method for viral prophylaxis or treatment in a subject, said method comprising administering to said subject an effective amount of a mutant *Salmonella* sp. comprising a genetically modified msbB gene and a mutation characterized by increased growth when grown in acidified media compared to the msbB− mutant *Salmonella* designated YS1646 having ATCC Accession No. 202165. In accordance with these embodiments, the mutant *Salmonella* sp. further comprise one or more genetically modified genes to auxotrophy and/or one or more nucleic acid molecules encoding one or more therapeutic molecules.

In a preferred embodiment, the present invention provides a method of prophylaxis or treatment of virally induced disease in a subject, said method comprising administering to said subject an effective amount of a mutant *Salmonella* sp. comprising a genetically modified msbB gene and a genetically modified zwf gene. In accordance with this embodiment, the mutant *Salmonella* sp. may further comprise one or more genetically modified genes to auxotrophy and/or one or more nucleic acid molecules encoding one or more therapeutic molecules.

In a preferred embodiment of the invention, the bacteria have genetic modifications which result in the expression of at least one hemagglutinin and/or one neuraminidase, where each gene is optimized for bacterial expression in at least one codon. In a most preferred embodiment, the hemagglutinin and/or neuraminidase genes are further modified to be secreted by the bacteria as heterologous fusion proteins. In a most preferred embodiment, the neuraminidase and hemagglutinin heterologous fusion proteins are integrated into the chromosome in delta IS200 sites.

In a preferred embodiment, the bacterial strains are genetically stabilized by deletion of IS200 elements, which reduces their genetic recombination potential.

In another embodiment, the bacterial strains are genetically stabilized by deletion of phage and prophage elements, which reduces their genetic recombination and transduction potential.

In another embodiment, the bacterial strains are genetically isolated from phage infection by constitutive expression of the P22 C2 repressor, which reduces their ability to be infected by phage and the subsequent transduction of genes by such phage.

In another embodiment, the bacterial strains have genetically defined flagellar antigens, or no flagellar antigens, which reduces the immune system elimination of the vector, enhancing its immunization potential in second immunizations.

In a preferred embodiment, the genetically modified bacteria are used in animals, including humans, birds, dogs and pigs, for protection against avian influenza and highly pathogenic derivatives.

In another embodiment, a kit allows for rapid construction of a bacterial vaccine which is closely matched to an emerging avian influenza or its highly pathogenic derivative.

In another embodiment, the invention provides a bacterium capable of having it's growth inhibited by gluconate and a method of controlling bacterial growth by means of administering gluconate. In a preferred embodiment, the bacterium capable of having it's growth inhibited by gluconate is deficient in both the msbB and zwf genes.

The live attenuated bacteria described by Bermudes WO/2008/039408 are designed to achieve a close antigenic match between the vaccine strain and the target strain. Bermudes targets viruses for vaccine strains based on their emerging pathogenicity, and produces an effective vaccine more closely matched to the antigen profile of the emerging pathogen. As Bermudes requires detailed knowledge of the antigenic profile of an emerging strain, such a vaccine can be produced at the time of need in order to reduce the risk of an unmatched vaccine and potential effects of partial protection in a human pandemic outbreak. Thus Bermudes provides vaccines for protecting a human patient against infection by an emerging avian influenza virus strain.

Accordingly, when orally or nasally administered to an individual, a live *Salmonella* bacterial vaccine, in accordance with the present invention, that is genetically engineered to express one or more avian influenza antigens as described herein and having a first attenuating mutation that reduces TNF-α induction and confers sensitivity to $CO_2$, osmolarity and/or acidic pH and a second mutation that confers resistance to $CO_2$, osmolarity and/or acidic pH and restores their ability to grow therein without increasing TNF-α induction and have improved ability to establish a population (infection) in the nasopharyngeal and/or bronchial/pulmonary or gut tissues and, if properly modified they could provide a desirable source of immunogenic avian influenza antigen polypeptide(s) to elicit an immune response in the mucosal tissue of the individual.

The antigen(s) can invoke an antibody and/or cellular immune responses in the patient that are capable of neutralizing the emerging avian influenza vaccine strains with high efficiency, as well as emerging heterologous avian influenza vaccine strains, with moderate efficiency. Preferably, the emerging avian influenza vaccine will be within the same hemagglutinin and or neuraminidase type (i.e., H1, H5, H5 (H274Y), H7 or H9 and/or N1, N2 or N7) as are the current pathogenic avian influenza strains.

The live vaccine compositions are suitable for oral administration to an individual to provide protection from avian influenza. Preferably, a vaccine composition comprises a suspension of a live bacterial strain described herein in a physiologically accepted buffer or saline solution that can be swallowed from the mouth of an individual. However, oral administration of a vaccine composition to an individual may also include, without limitation, administering a suspension of a bacterial vaccine strain described herein through a nasojejunal or gastrostomy tube and administration of a suppository that releases a live bacterial vaccine strain to the lower intestinal tract of an individual. Vaccines of the invention may be formulated for delivery by other various routes e.g. by intramuscular injection, subcutaneous delivery, by intranasal delivery (e.g. WO 00/47222, U.S. Pat. No. 6,635, 246), intradermal delivery (e.g. WO02/074336, WO02/067983, WO02/087494, WO02/0832149 WO04/016281) by transdermal delivery, by transcutaneous delivery, by topical routes, etc. Injection may involve a needle (including a microneedle), or may be needle-free.

Vaccines of the invention use one or more avian antigens to protect patients against infection by an influenza virus strain that is capable of human-to-human transmission i.e. a strain that will spread geometrically or exponentially within a given human population without necessarily requiring physical contact. The patient may also be protected against strains that infect and cause disease in humans, but that are caught from birds rather than from other humans (i.e., bird to human transmission). The invention is particularly useful for protecting against infection by pandemic, emerging pandemic and future pandering human strains e.g. for protecting against H5 and N1 influenza subtypes. Depending on the particular season and on the nature of the antigen included in the vaccine, however, the invention may protect against any hemagglutinin subtypes, including H1, H2, H3, H4, H5, H6, H7, H8, H9, H10, H11, H12, H13, H14, H15 or H16 or various neuraminidase subtypes, including N1, N2, N3, N4, N5, N6, N7, N8 or N9.

The characteristics of an influenza strain that give it the potential to cause a pandemic outbreak may include: (a) it contains a new or antigenically altered hemagglutinin compared to the hemagglutinins in currently-circulating human strains i.e., one that has not been evident in the human population for over a decade (e.g. H2), or has not previously been seen at all in the human population (e.g. H5, H6 or H9, that have generally been found only in bird populations), such that the human population will be immunologically naive to the strain's hemagglutinin or that is a subtype which is antigenically altered by changes in amino acid sequence or glycosylation; (b) it is capable of being transmitted horizontally in the human population; (c) is capable of being transmitted from animals (including birds, dogs, pigs) to humans; and/or (d) it is pathogenic to humans.

As a preferred embodiment of the invention protects against a strain that is capable of human-to-human or bird-to-human or bird-to-bird transmission, one embodiment of the invention in accordance with that aspect will generally include at least one gene that originated in a mammalian (e.g. in a human) influenza virus and one gene which originated in a bird or non-human vertibrate. Vaccines in accordance with various aspects of the invention may therefore include an antigen from an avian influenza virus strain. This strain is typically one that is capable of causing highly pathogenic avian influenza (HPAI). HPAI is a well-defined condition (Alexander Avian Dis (2003) 47(3 Suppl):976-81) that is characterized by sudden onset, severe illness and rapid death of affected birds/flocks, with a mortality rate that can approach 100%. Low pathogenicity (LPAI) and high pathogenicity strains are easily distinguished e.g. van der Goot et al. (Epidemiol Infect (2003) 131(2):1003-13) presented a comparative study of the transmission characteristics of low and high pathogenicity H5N2 avian strains. For the 2004 season, examples of HPAI strains are H5N1 influenza A viruses e.g. A/Viet Nam/I 196/04 strain (also known as A Vietnam/3028/2004 or A/Vietnam/3028/04). The skilled person will thus be able to identify or predict future HPAI strains and the DNA sequence and amino acid compositions of the H and N antigens as and when they emerge. The avian influenza strain may be of any suitable hemagglutinin subtype, including H1, H2, H3, H4, H5, H6, H7, H8, H9, H10, H11, H12, H13, H14, H15 or H16. The avian influenza strain may further be of any suitable neuraminidase subtype N1, N2, N3, N4, N5, N6, N7, N8, or N9. The vaccines of the invention may comprise two or more (i.e., two, three, four, or five) avian influenza hemagglutinin and neuraminidase antigens. Such avian influenza strains may comprise the same or different hemagglutinin subtypes and the same or different neuraminidase subtypes.

A preferred vaccine composition will contain a sufficient amount of live bacteria expressing the antigen(s) to produce an immunological response in the patient. Accordingly, the attenuated stress-resistant *Salmonella* strains described herein are both safe and useful as live bacterial vaccines that can be orally administered to an individual to provide immunity to avian influenza and, thereby, protection from avian influenza.

Although not wishing to be bound by any particular mechanism, an effective mucosal immune response to avian influenza antigen(s) in humans by oral administration of genetically engineered, attenuated strains of *Salmonella* strains as described herein may be due to the ability of such mutant strains to pass through the acidic environment of the stomach and persist in the intestinal tract which is known to contain high levels of $CO_2$ and to exhibit acidic pH (Jensen and Jorgensen, Applied and Environmental Microbiology 60: 1897-1904) before accessing the gut mucosa, gut lymphoidal cells and/or gut dendridic cells. Each bacterial strain useful in the invention carries an antigen-expressing plasmid or chromosomally integrated cassette that encodes and directs expression of one or more avian influenza antigens of avian influenza virus when resident in an attenuated *Salmonella* strain described herein. As noted above, avian influenza antigens that are particularly useful in the invention include an H1, H5, H5 (H274Y), H7 or H9 antigen polypeptide (or immunogenic portion thereof), a N1, N2 or N7 antigen polypeptide (or immunogenic portion thereof), and a fusion polypeptide comprising a heterologous secretion peptide linked in-frame to the antigenic peptide.

The serovars of *S. enterica* that may be used as the attenuated bacterium of the live vaccine compositions described herein include, without limitation, *Salmonella enterica* serovar *Typhimurium* ("*S. typhimurium*"), *Salmonella montevideo*, *Salmonella enterica* serovar *Typhi* ("*S. typhi*"), *Salmonella enterica* serovar *Paratyphi* B ("*S. paratyphi* 13"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorurn* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anaturn* ("*S. anatum*"), *Salmonella enterica* serovar *Dublin* ("*S. dublin*"), *Salmonella enterica* serovar *Derby* ("*S.

derby"), *Salmonella enterica* serovar *Choleraesuis* var. *kunzendorf* ("*S. cholerae kunzendorf*"), and *Salmonella enterica* serovar *minnesota* ("*S. Minnesota*").

By way of example, live avian influenza vaccines in accordance with aspects of the invention include known strains of *S. enterica* serovar *Typhimurium* (*S. typhimurium*) and *S. enterica* serovar *Typhi* (*S. typhi*) which are further modified as provided by the invention to form suitable vaccines for the prevention and treatment of avian influenza. Such Strains include Ty21a, CMV906, CMV908, CMV906-htr, CMV908-htr, Ty800, aroA-/serC-, holavax, M01ZH09, VNP20009.

Novel strains are also encompassed that are attenuated in virulence by mutations in a variety of metabolic and structural genes. The invention therefore may provide a live vaccine composition for protecting against avian influenza comprising a live attenuated bacterium that is a serovar of *Salmonella enterica* comprising, an attenuating mutation in a genetic locus of the chromosome of said bacterium that attenuates virulence of said bacterium and wherein said attenuating mutation is the Suwwan deletion (Murray et al., 2004, Journal of Bacteriology 186: 8516-8523) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, purA, purB, purI, purF, aroA, aroB, aroC, aroD, serC, gua, cadA, rfc, rjb, rfa, ompR, msbB and combinations thereof.

The invention may also be incorporated into a process for preparing genetically stable bacterial vaccines for protecting a human patient against infection by a avian influenza virus strain, comprising genetically engineering the avian antigen from an avian influenza virus strain that can cause highly pathogenic avian influenza to comprise a bacterially codon optimized expression sequence within a bacterial plasmid expression vector or chromosomal localization expression vector and further containing engineered restriction endonuclease sites such that the bacterially codon optimized expression gene contains subcomponents which are easily and rapidly exchangeable in order to facilitate rapid exchange of the genetic subcomponents to achieve a well matched antigen to the emerging avian influenza pathogen. The plasmid and/or chromosomal expression constructs may be further modified to result in the secretion of the viral antigens. Administration of the vaccine to the patient invokes an antibody and/or cellular immune response that is capable of neutralizing said avian influenza virus strain.

The invention may also be incorporated into methods and compositions for producing a bacterial vector expressing one or more avian influenza antigens where said bacterial vector has one or more deletions in IS200 elements which results in enhance genetic stability. The composition and methods comprise a bacterial strain with a deletion in the IS200 elements, such that the bacteria are no longer capable of genetic rearrangement using IS200 elements. Such a deletion is generated in any one or more IS200 element, which is then confirmed using standard genetic techniques.

The invention may also be incorporated into methods and compositions for producing a genetically stabilized bacterial vector expressing one or more avian influenza antigens where said bacterial vector has one or more deletions in bacteria phage or prophage elements which enhanced genetic stability and prevent phage excision. The composition and methods comprise a bacterial strain with one or more deletions in bacteria phage or prophage elements, such that the bacteria are no longer capable of genetic rearrangement using bacteria phage or prophage elements. Such a deletion is generated in any bacteria phage or prophage elements, which is then confirmed using standard genetic techniques. Such strains have phage with reduced capacity for transduction of genes to other strains.

The invention may also be incorporated into methods and compositions for producing a bacterial vector expressing one or more avian influenza antigens where said bacterial vector constitutively expresses the P22 phage C2 repressor, thereby preventing new infections by bacteria phage and further preventing subsequent phage transductions by these phage.

The invention may also be incorporated into live *Salmonella* vaccines having had deletions of the hin gene and/or defined fH1 or fH2 antigens, or may have been constructed such that they lack fH antigens altogether. The invention may also make use of *Salmonella* strains expressing non-overlapping O-antigens, such as those of *S. typhimurium* (O-1, 4, 5, 12) *S. typhi* is (Vi), or *S. montevideo* (O-6, 7). Changing of the outer coat may be accomplished by genetic manipulations known to those skilled in the arts. Both antigenic changes may be used together. Accordingly, the invention may also be incorporated into live *Salmonella* vaccines constructed to maximize a prime-boost strategy which alternates or eliminates the fH antigen whereby the immune response of the fH antigen of the first immunization (prime) is not specific for the antigen of the second immunization (boost) and likewise, the O antigen profile of the first immunization is not the same for the second immunization. Therefore, the boost immunization is not diminished by a rapid elimination by the immune system, and is therefore able to persist longer and more effectively present the immunizing heterologous avian influenza antigen.

An embodiment of the present invention therefore may also be incorporated into methods and compositions for producing a bacterial vector expressing one or more avian influenza antigens where said bacterial vector has a defined flagellar H antigen (fH). The composition and methods comprise a bacterial strain with a deletion in the Hin recombinase gene, such that the bacteria are no longer capable of alternating between fH1 and fH2 antigens. Such a deletion is generated in either an fH1 or fH2 serologically defined strain, which is then reconfirmed following deletion or disruption of the hin recombinase gene. The invention may also be incorporated into methods and compositions for producing a bacterial vector which lacks flagellar antigens generated by deletion of the fliBC genes (i.e., fH0). Therefore, an improved composition for a prime/boost strategy is provided where the second vaccination comprises administration of a vaccine where the fH antigen composition is different from the first vaccination. In the case where the antigen is presented as a fusion with the fliC gene, preferably only fH1 and fH2 forms are utilized; fH0 is preferably not used.

The invention may also may also be incorporated into a method for protecting a human patient against infection by an avian influenza virus strain with an improved prime/boost strategy, comprising the step of administering to the patient a vaccine that comprises an antigen from an avian influenza virus strain that can cause highly pathogenic avian influenza or 1918 influenza within a bacterial vector expressing one or more avian influenza antigens where said bacterial vector has a defined fH antigen or no fH antigen (i.e., fH1, fH2, or fH0) and/or various non-overlapping O-antigens. The invention may further may also be incorporated into a method of administering a second bacterial vector expressing one or more avian influenza antigens comprising a second step where the second administration where said bacterial vector has a defined fH antigen which is different fH antigen composition than the fH antigen of the first administration or no fH antigen. The second administration includes a bacterial vaccine where the first vaccine administration is a bacterial vaccine of the present invention or is another vaccine not encompassed by the present application, e.g., another bacterial vaccine or an egg-based vaccine.

Similarly, the invention may also may also be incorporated into a kit comprising (a) a first container comprising a bacterial expression codon optimized antigen from a pathogenic avian influenza virus strain containing unique genetically engineered restriction sites contained within either a bacterial protein expression plasmid or a bacterial chromosomal protein expression vector and (b) a second container comprising bacterial vector(s) with one or more (e.g., fH1, fH2 or fH0) flagellar antigen(s) and/or various non-overlapping O-antigens. Component (a) will be modifiable to genetically match an emerging avian influenza virus using standard in vitro molecular techniques and can be combined with component (b) to generate one or more bacterial strains with defined flagellar antigens which constitute a live vaccine. The variation(s) in flagellar antigens provided by the kit provide for more than one live vaccine strain in which a first immunization (prime) using one strain may be followed at an appropriate time such as 2 to 4 weeks by a second immunization (boost) using a second strain with a different fH antigen or no fH antigen. The live vaccine compositions are suitable for oral or nasal administration to an individual to provide protection from avian influenza.

Preferably, the invention may also be incorporated into a vaccine composition comprising a suspension of a live bacterial strain described herein in a physiologically accepted buffer or saline solution that can be swallowed from the mouth of an individual. However, oral administration of a vaccine composition to an individual may also include, without limitation, administering a suspension of a bacterial vaccine strain described herein through a nasojejunal or gastrostomy tube and administration of a suppository that releases a live bacterial vaccine strain to the lower intestinal tract of an individual.

4. DEFINITIONS

In order that the invention may be more fully understood, the following terms are defined.

$CO_2$ conditions: As used herein, the term "$CO_2$ conditions" refers to $CO_2$ levels above ambient air. In particular, the term "$CO_2$ conditions" refers to $CO_2$ levels above 0.3%, 0.4%, 0.45%, 0.5%, 0.75%, 1%, 1.5%, 2%, 2.5%, 3%, 3.5%, 4%, 4.5%, 5% or higher.

High osmolarity: As used herein, the term "high osmolarity" refers to osmolarity above the growth-permissive osmolarity level of LB-O and or MSB media described in the examples of approximately 100 milliosmoles, normal physiological osmolarity found in a subject (approximately 300 milliosmoles), particular, to the osmolarity found in an organ or tissue of a subject. In certain embodiments, the term "high osmolarity" refers to osmolarity above approximately 340 millosmoles, 450 millosmoles, 475 millosmoles, 500 millosmoles, 525 millosmoles, 550 millosmoles, 575 millosmoles, 600 millosmoles or more. In certain embodiments, the term the osmolarity-resistant gram-negative mutants are sensitive to normal physiological osmolarity found in a subject.

Pentose Phosphate Pathway: The pentose phosphate pathway (also called Phosphogluconate Pathway, or Hexose Monophosphate Shunt [HMP shunt]: see Fraenkel 1996, Glycolysis, In Neidhardt (ed) *Escherichia coli* and *Salmonella*, Second Ed., ASM Press, Washington, D.C., pp. 189-198, expressly incorporated by reference herein) is a process that serves to generate NADPH and the synthesis of pentose (5-carbon) sugars. There are two distinct phases in the pathway. The first is the oxidative phase, in which NADPH is generated, and the second is the non-oxidative synthesis of 5-carbon sugars. This pathway is an alternative to glycolysis. While it does involve oxidation of glucose, its primary role is anabolic rather than catabolic. The primary functions of the pathway are: 1) To generate reducing equivalents, in the form of NADPH, for reductive biosynthesis reactions within cells; 2) to provide the cell with ribose-5-phosphate (R5P) for the synthesis of the nucleotides and nucleic acids; and 3) to metabolize pentose sugars derived from the digestion of nucleic acids as well as to rearrange the carbon skeletons of carbohydrates into glycolytic/gluconeogenic intermediates.

Gene comprising the pentose phosphate pathway include zwf (glucose 6-phosphate dehydrogenase, EC 1.1.1.49), pgl (6-phosphogluconolactonase, EC 3.1.1.31), gnd (6-phosphogluconate dehydogenase, EC 1.1.1.4), rpe (ribulose phosphate 3-epimerase, EC 5.1.3.1), rpiA/rpiB (ribose-5-phosphate isomerase A & B, EC 5.3.1.6), tktA/tktB (transkeolase A & B. EC 2.2.1.1), and talA/talB (transaldolase A & B, EC 2.2.1.2). Additionally, related gene products that provide gluconate into the pentose pathway, gntT and other transporters for gluconate including the homologous gntU, gntP and idnT transporters are encompassed.

Stress-resistant gram-negative bacterial mutants: As used herein, the "stress-resistant gram-negative bacterial mutants" and variations thereof refer to gram-negative bacteria with the ability to grow under one or more environmental stresses such as may exist in the body of an animal (mammal, bird, reptile). Examples of environmental stresses include, but are not limited to, $CO_2$ concentration, temperature, pH, and osmolarity. Stress-resistant gram-negative bacterial mutants include, but are not limited to, gram-negative bacteria that are resistant to $CO_2$ and/or acid pH. In a preferred embodiment, stress-resistant gram-negative mutants are attenuated. In another preferred embodiment, stress-resistant gram-negative mutants have one or more mutations in lipid metabolism, in particular, LPS biosynthesis. In a specific embodiment, stress-resistant gram-negative mutants are stress-resistant *Salmonella* sp. In a preferred embodiment, stress-resistant gram-negative mutants are attenuated stress-resistant *Salmonella* sp.

As used herein, "attenuated", "attenuation", and similar terms refer to elimination or reduction of the natural virulence of a bacterium in a particular host organism, such as a mammal. "Virulence" is the degree or ability of a pathogenic microorganism to produce disease in a host organism. A bacterium may be virulent for one species of host organism (e.g., a mouse) and not virulent for another species of host organism (e.g., a human). Hence, broadly, an "attenuated" bacterium or strain of bacteria is attenuated in virulence toward at least one species of host organism that is susceptible to infection and disease by a virulent form of the bacterium or strain of the bacterium. As used herein, the term "genetic locus" is a broad term and comprises any designated site in the genome (the total genetic content of an organism) or in a particular nucleotide sequence of a chromosome or replicating nucleic acid molecule (e.g., a plasmid), including but not limited to a gene, nucleotide coding sequence (for a protein or RNA), operon, regulon, promoter, regulatory site (including transcriptional terminator sites, ribosome binding sites, transcriptional inhibitor binding sites, transcriptional activator binding sites), origin of replication, intercistronic region, and portions therein. A genetic locus may be identified and characterized by any of a variety of in vivo and/or in vitro methods available in the art, including but not limited to, conjugation studies, crossover frequencies, transformation analysis, transfection analysis, restriction enzyme mapping protocols, nucleic acid hybridization analyses, polymerase chain reaction (PCR) protocols, nuclease protection assays, and direct nucleic acid sequence analysis. As used herein, the term "infection" has the meaning generally used and understood by persons skilled in the art and includes the invasion and multiplication of a microorganism in or on a host organism ("host", "individual", "patient") with or without a manifestation of a disease (see, "virulence" above). Infectious microorganisms include pathogenic viruses, such as avian influenza, that can cause serious diseases when infecting an unprotected individual. An infection may occur at one or more sites in or on an individual. An infection may be unintentional (e.g., unintended ingestion, inhalation, contamination of wounds, etc.) or intentional (e.g., administration of a live vaccine strain, experimental challenge with a pathogenic vaccine strain). In a vertebrate host organism, such as a mammal, a site of infection includes, but is not limited to, the respiratory system, the alimentary canal (gut), the circulatory system, the skin, the endocrine system, the neural system, and intercellular spaces. Some degree and form of replication or multiplication of an infective microorganism is required for the microorganism to persist at a site of infection. However, replication may vary widely among infecting microorganisms. Accordingly, replication of infecting microorganisms comprises, but is not limited to, persistent and continuous multiplication of the microorganisms and transient or temporary maintenance of microorganisms at a specific location. Whereas "infection" of a host organism by a pathogenic microorganism is undesirable owing to the potential for causing disease in the host, an "infection" of a host individual with a live vaccine comprising genetically altered, attenuated *Salmonella* bacterial strain as described herein is desirable because of the ability of the bacterial strain to elicit a protective immune response to antigens of avian influenza virus that cause avian influenza in humans and other mammals.

As used herein, the terms "disease" and "disorder" have the meaning generally known and understood in the art and comprise any abnormal condition in the function or well being of a host individual. A diagnosis of a particular disease or disorder, such as avian influenza, by a healthcare professional may be made by direct examination and/or consideration of results of one or more diagnostic tests.

A "live vaccine composition", "live vaccine", "live bacterial vaccine", and similar terms refer to a composition comprising a strain of live *Salmonella* bacteria that expresses at least one antigen of avian influenza, e.g., the H antigen, the N antigen, or a combination thereof, such that when administered to an individual, the bacteria will elicit an immune response in the individual against the avian influenza antigen(s) expressed in the *Salmonella* bacteria and, thereby, provide at least partial protective immunity against avian influenza. Such protective immunity may be evidenced by any of a variety of observable or detectable conditions, including but not limited to, diminution of one or more disease symptoms (e.g., respiratory distress, fever, pain, diarrhea, bleeding, inflammation of lymph nodes, weakness, malaise), shorter duration of illness, diminution of tissue damage, regeneration of healthy tissue, clearance of pathogenic microorganisms from the individual, and increased sense of well being by the individual. Although highly desired, it is understood by persons skilled in the art that no vaccine is expected to induce complete protection from a disease in every individual that is administered the vaccine or that protective immunity is expected to last throughout the lifetime of an individual without periodic "booster" administrations of a vaccine composition. It is also understood that a live vaccine comprising a bacterium described herein may be, at the discretion of a healthcare professional, administered to an individual who has not presented symptoms of avian influenza but is considered to be at risk of infection or is known to already have been exposed to avian influenza virus, e.g., by proximity or contact with avian influenza patients or virally contaminated air, liquids, or surfaces.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "recombinant" is used to describe non-naturally altered or manipulated nucleic acids, cells transformed, electroporated, or transfected with exogenous nucleic acids, and polypeptides expressed non-naturally, e.g., through manipulation of isolated nucleic acids and transformation of cells. The term "recombinant" specifically encompasses nucleic acid molecules that have been constructed, at least in part, in vitro using genetic engineering techniques, and use of the term "recombinant" as an adjective to describe a molecule, construct, vector, cell, polypeptide, or polynucleotide specifically excludes naturally existing forms of such molecules, constructs, vectors, cells, polypeptides, or polynucleotides.

Cassette, or expression cassette is used to describe a nucleic acid sequence comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter. The cassette may also contain a multiple cloning site (MCS) and transcriptional terminator within the 5' and 3' restriction endonuclease cleavage sites. The cassette may also contain cloned genes of interest.

As used herein, the term "*salmonella*" (plural, "salmonellae") and "*Salmonella*" refers to a bacterium that is a serovar of *Salmonella enterica*. A number of serovars of *S. enterica* are known. Particularly preferred *salmonella* bacteria useful in the invention are attenuated strains of *Salmonella enterica* serovar *Typhimurium* ("*S. typhimurium*") and serovar *Typhi* ("*S. typhi*") as described herein. As used herein, the terms "strain" and "isolate" are synonymous and refer to a particular isolated bacterium and its genetically identical progeny. Actual examples of particular strains of bacteria developed or isolated by human effort are indicated herein by specific letter and numerical designations (e.g. strains Ty21a, CMV906, CMV908, CMV906-htr, CMV908-htr, Ty800, holavax, M01ZH09, VNP20009).

The definitions of other terms used herein are those understood and used by persons skilled in the art and/or will be evident to persons skilled in the art from usage in the text. This invention provides live vaccine compositions for protecting against avian influenza comprising live *Salmonella enterica* serovars that are genetically engineered to express one or more avian influenza antigen polypeptides, such as the H1, H5, H5 (H274Y), H7 or H9 and N1, N2 and N7 antigens of avian influenza virus.

5. BRIEF DESCRIPTION OF THE DRAWINGS

FIGS. 3A, 3B, 3C and 3D show msbB− confers growth-sensitivity in liquid media under $CO_2$ conditions containing physiological amounts of salt and is suppressed by zwf.

FIGS. 5A, 5B, 5C, and 5D show that zwf suppresses growth sensitivity to acidic pH in LB broth in both ambient air and 5% $CO_2$.

FIGS. 6A and 6B show a β-galactosidase release assays confirm cell lysis in LB broth, pH 6.6 and that zwf confers resistance.

Figure 7:
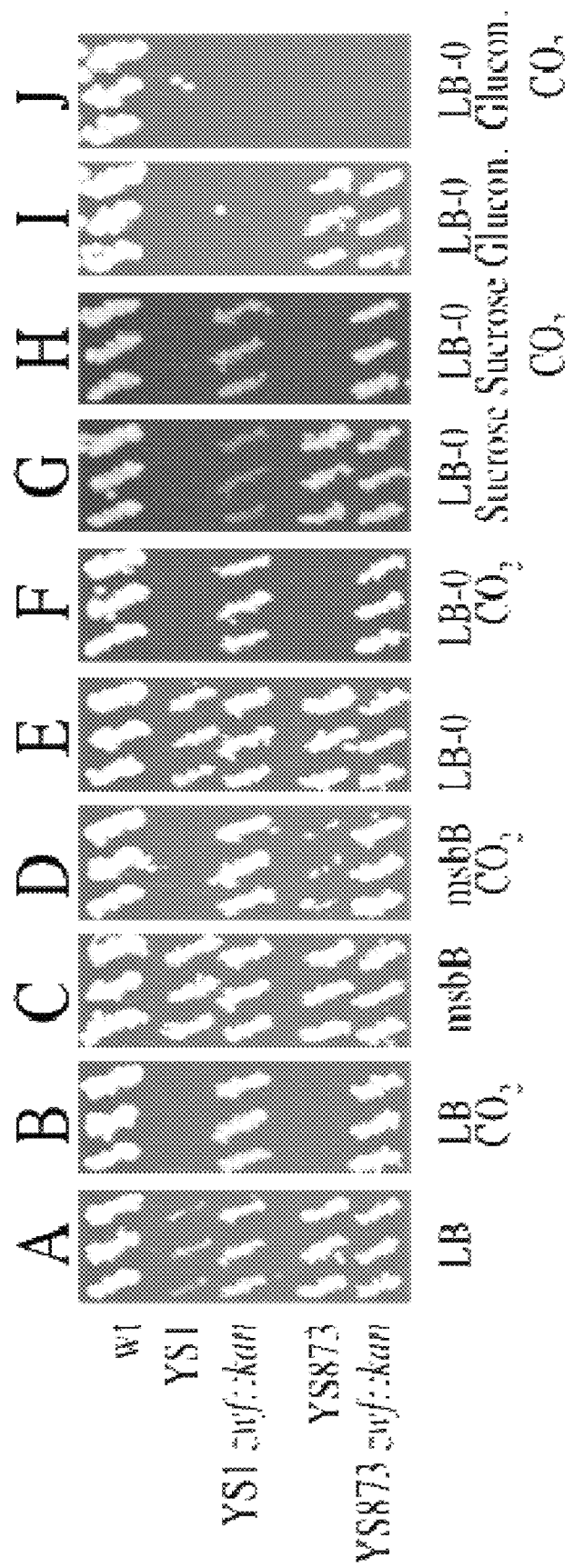

FIG. 7 shows a series of replica plate results for different strains on different media showing zwf mutation suppresses both msbB-induced $CO_2$ sensitivity and osmotic defects.

Figure 8:
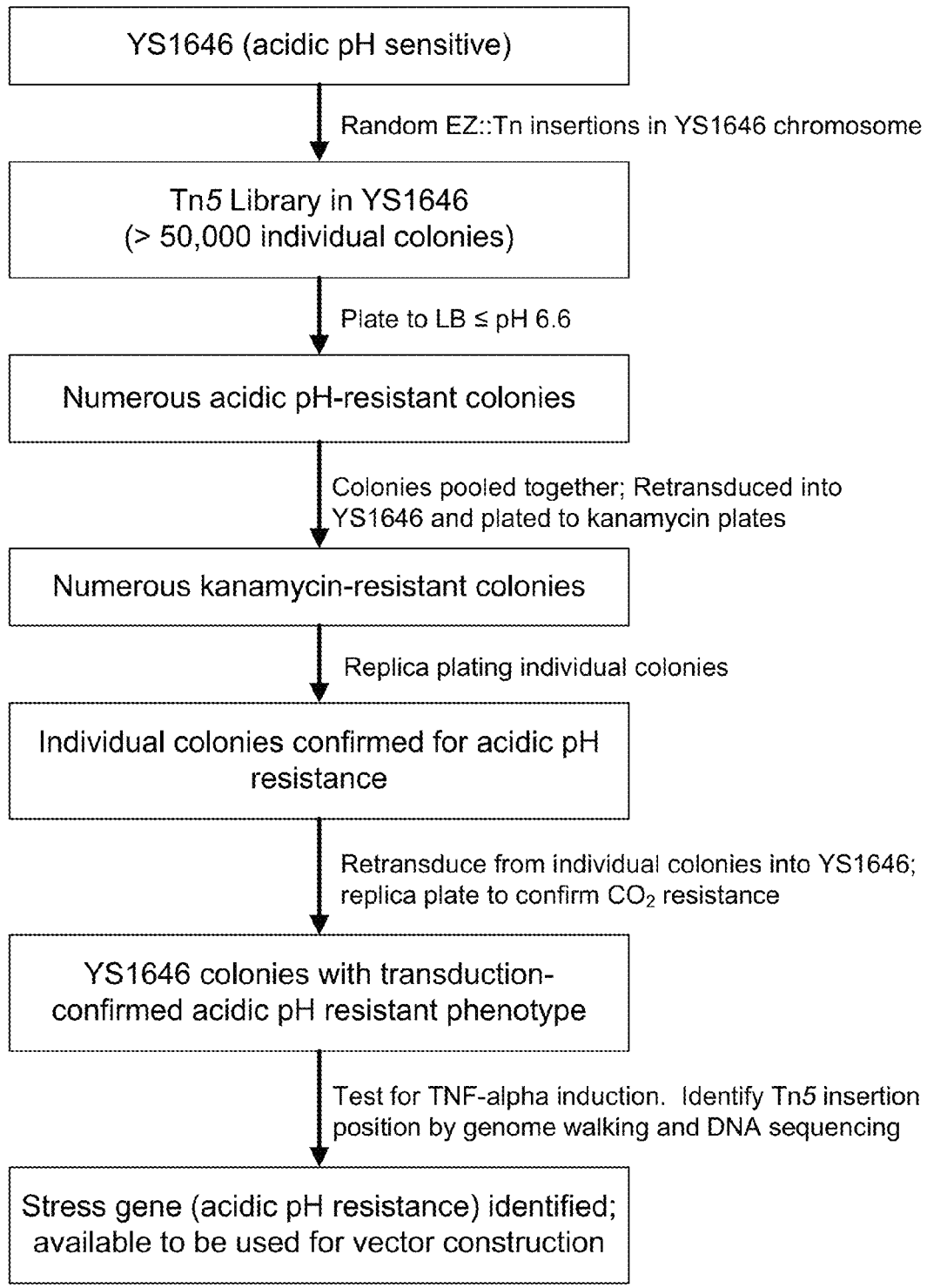

FIG. 8 shows a flow chart depicting the selection scheme for isolation of transposon insertions used to isolate acidic pH-resistant mutants.

Figure 9:
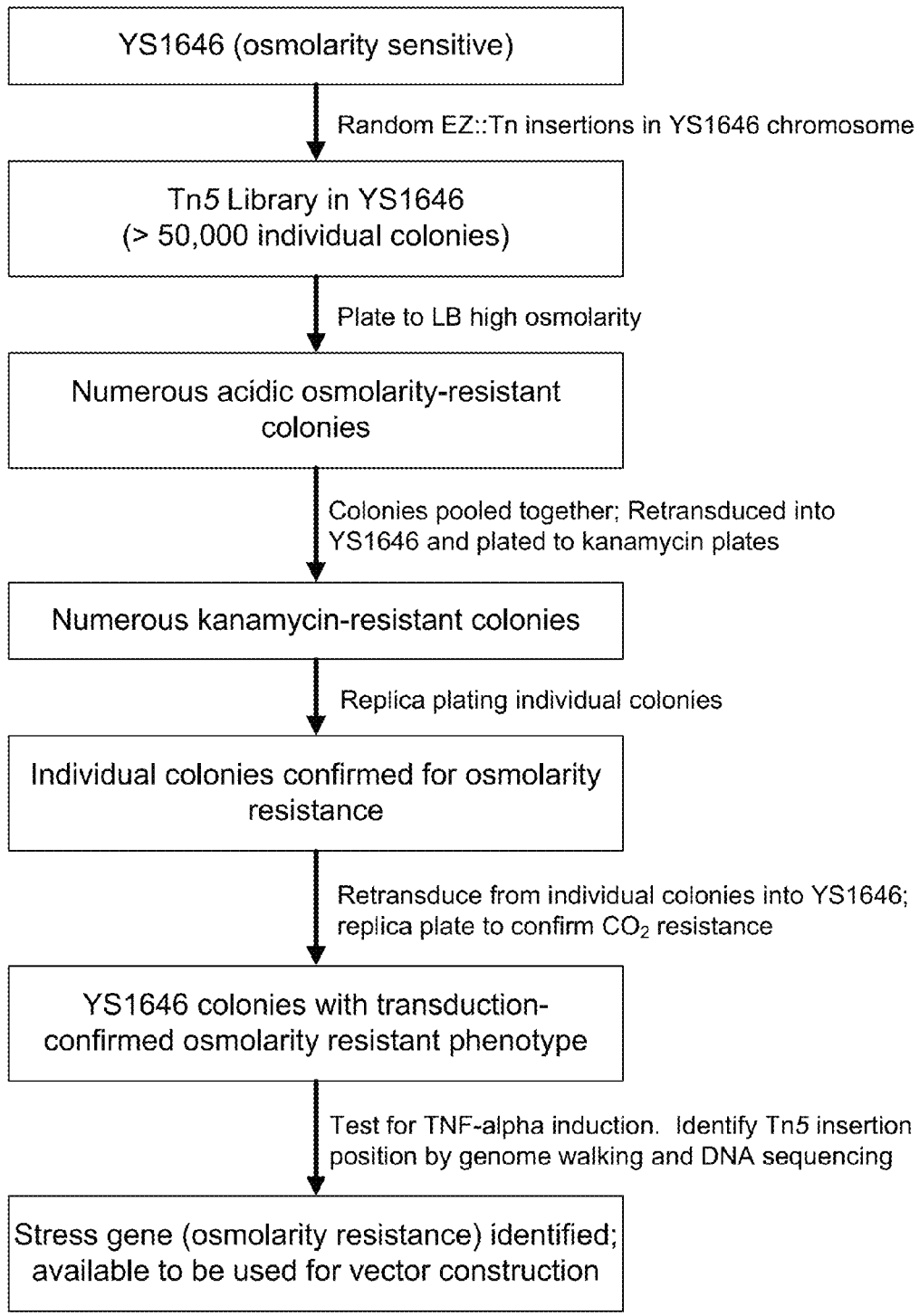

FIG. 9 shows a flow chart depicting the selection scheme for isolation of transposon insertions used to isolate osmolarity-resistant mutants.

6. DETAILED DESCRIPTION OF THE INVENTION

The invention provides gram-negative bacterial mutants resistant to one or more stress conditions, including, but not limited to, $CO_2$, acid pH, and/or high osmolarity. In one embodiment, the present invention provides gram-negative bacterial mutants resistant to $CO_2$, acid pH, and/or high osmolarity. In a more preferred embodiment, the present invention provides attenuated gram-negative bacterial mutants resistant to $CO_2$, acid pH, and/or high osmolarity. Preferably, the stress-resistant gram-negative bacterial mutants are attenuated by introducing one or more mutations in one or more genes in the lipopolysaccharide (LPS) biosynthetic pathway that reduces the induction of TNF-α, and optionally, one or more mutations to auxotrophy for one or more nutrients or metabolites.

The invention also provides stress-resistant gram-negative bacterial mutants engineered to contain and/or express one or more nucleic acid molecules encoding one or more therapeutic molecules. In a specific embodiment, the present invention provides stress-resistant gram-negative mutants engineered to contain and/or express one or more nucleic acid molecules encoding one or more therapeutic molecules. In another embodiment, the present invention provides attenuated stress-resistant gram-negative mutants engineered to contain and/or express one or more nucleic acid molecules encoding one or more therapeutic molecules. In yet another preferred embodiment, the present invention provides attenuated stress-resistant gram-negative mutants engineered to contain and/or express one or more nucleic acid molecules encoding one or more therapeutic molecules.

The invention also provides pharmaceutical compositions comprising pharmaceutically acceptable carriers and one or more stress-resistant gram-negative bacterial mutants, preferably one or more stress-resistant gram-negative bacterial mutants. The invention also provides pharmaceutical compositions comprising pharmaceutically acceptable carriers and one or more stress-resistant gram-negative bacterial mutants, comprising nucleotide sequences encoding one or more therapeutic molecules. The pharmaceutical compositions of the invention may be used in accordance with the methods of the invention for prophylaxis or treatment of virally-induced disease. Preferably, the stress-resistant gram-negative bacterial mutants are attenuated by introducing one or more mutations in one or more genes in the lipopolysaccharide (LPS) biosynthetic pathway, and optionally one or more mutations to auxotrophy for one or more nutrients or metabolites.

The present invention encompasses treatment protocols that provide a better therapeutic effect than current existing vaccines. In particular, the present invention provides methods for prevention or treatment of virally-induced disease in a subject comprising administering to said subject and one or more stress-resistant gram-negative bacterial mutants. The present invention also provides methods for the for viral infection prophylaxis or treatment in a subject comprising administering to said subject one or more stress-resistant gram-negative bacterial mutants, preferably attenuated stress-resistant gram-negative bacterial mutants, wherein said stress-resistant gram-negative bacterial mutants comprise one or more nucleic acid molecules encoding one or more therapeutic molecules.

The present invention provides methods for the enhanced delivery of one or more therapeutic molecules for prophylaxis and treatment of virally-induced disease comprising administering to said subject one or more stress-resistant gram-negative bacterial mutants, comprising nucleic acid molecules encoding one or more therapeutic molecules. The methods of the present invention permit lower dosages and/or less frequent dosing of stress-resistant gram-negative bacterial mutants (preferably attenuated stress-resistant gram-negative bacterial mutants) to be administered to a subject for prophylaxis or treatment of virally-induced disease to achieve a therapeutically effective amount of one or more therapeutic molecules.

The invention also provides a pharmaceutical pack or kit comprising one or more containers with one or m ore of the components of the pharmaceutical compositions of the invention. The kit further comprises instructions for use of the composition(s). In certain embodiments of the invention, the kit comprises a document providing instructions for the use of the composition(s) of the invention in, e.g., written and/or electronic form. Said instructions provide information relating to, e.g., dosage, methods of administration, and duration of treatment. Optionally associated with such container(s) can be a notice in the form prescribed by a governmental agency regulating the manufacture, use or sale of pharmaceuticals or biological products which notice reflects approval by the agency of manufacture, use or sale for human administration.

For reasons of clarity, the detailed description is divided into the following subsections: Stress-Resistant Gram-Negative Bacterial Mutants; Production of Stress-Resistant Gram-Negative Bacterial Mutants; Identification and Selection of Stress-Resistant Gram-Negative Bacterial Mutants; Genetic Modifications to Stress-Resistant Mutants with Transposon Insertions or Multicopy Plasmids; Therapeutic Molecules; Expression Vehicles Methods and Compositions for Delivery; Methods of Determining the Therapeutic Utility; and Kits.

6.1. Stress-Resistant Gram-Negative Bacterial Mutants

Any gram-negative bacterial with the ability to grow under one or more environmental stresses such as those that exist in animals (i.e., stress-resistant gram-negative bacterial mutants) may be used in the compositions and methods of the invention. Examples of environmental stresses include, but are not limited to, $CO_2$ resistant, acid pH resistant, and/or osmolarity resistant gram-negative bacterial mutants (methods for identifying, isolating, and producing such gram-negative bacterial are described infra). In a specific embodiment, the gram-negative bacteria used in the compositions and methods of the invention are $CO_2$ resistant and/or acid pH resistant gram-negative bacterial mutants.

In a preferred embodiment, the stress-resistant gram-negative bacterial mutants used in the compositions and methods of the invention are attenuated. Any technique well-known to one of skill in the art may be used to attenuate the stress-resistant gram-negative bacterial mutants. Preferably, the stress-resistant gram-negative bacterial mutants used in the compositions and methods of the invention are attenuated by the introduction of one or more mutations in one or more genes in the lipopolysaccharide (LPS) biosynthetic pathway, and optionally, one or more mutations to auxotrophy for one or more nutrients or metabolites. Examples of genes in the LPS biosynthetic pathway which may be attenuated include, but are not limited to, htrB, msbB, kdsA, kdsB, kdtA, lpxB, lpxC, and lpxD. Mutations to auxotrophy can be produced by the introduction of one or more mutations in a gene in a biosynthetic pathway such as the leucine, isoleucine, valine, phenylalanine, tryptophan, tyrosine, arginine, uracil, or purine biosynthetic pathway. In particular, a mutation in the AroA gene can result in auxotrophy. The attenuated stress-resistant gram-negative bacterial mutants induce lower levels of tumor necrosis factor-$\alpha$ (TNF-$\alpha$) than their wild-type counterpart (i.e., about 5% to about 40%, about 5% to about 35%, about 5% to about 25%, about 5% to about 15%, or about 5% to about 10% of TNF-$\alpha$ induced by wild-type) as measured by techniques well-known in the art (e.g., immunoassays such as ELISAs), and thus, avoid or reduce the risk of inducing septic shock in a subject administered a mutant bacterium for viral infection prophylaxis or treatment to said subject in accordance with the methods of the invention.

In a preferred embodiment, the stress-resistant gram-negative bacterial mutants used in the compositions and methods of the invention induce an immune response to avian influenza. The present invention encompasses compositions and methods for prophylaxis and treatment of virally-induced disease using stress-resistant gram-negative bacterial mutant which replicates at physiological temperatures (i.e., 35° C. to 44° C.) and induce an immune response in vitro or in vivo. Preferably, such bacteria inhibit or reduce viral burden in vivo. In accordance with the invention, such a gram-negative bacterial mutant may be engineered to contain or express one or more therapeutic molecules which have an anti-viral immunostimulatory activity in vivo.

While the teachings in sections of this application may refer specifically to *Salmonella*, the compositions and methods of the invention are in no way meant to be restricted to *Salmonella* but encompass any other gram-negative bacterium to which the teachings apply. Suitable bacteria which may be used in accordance with the invention include, but are not limited to, *Escherichia coli* including enteroinvasive *Escherichia coli* (e.g., enteroinvasive *Escherichia coli*), *Shigella* sp., and *Yersinia enterocohtica*. Thus, the reference to *Salmonella* in this application is intended to serve as an illustration and the invention is not limited in scope to *Salmonella*.

The present invention encompasses the use of *Salmonella* with the ability to grow under one or more environmental stresses such as those that exist within the body of an animal (i.e., stress-resistant *Salmonella* mutants) in the compositions and methods of the invention. Examples of environmental stresses include, but are not limited to, $CO_2$ concentration, temperature, pH, and osmolarity. Preferably, the *Salmonella* used in the compositions and methods of the invention are $CO_2$ resistant, acid pH resistant, and/or osmolarity resistant gram-negative bacterial mutants (methods for identifying, isolating, and producing such *Salmonella* are described infra). In a specific embodiment, the *Salmonella* used in the compositions and methods of the invention are $CO_2$ resistant and/or acid pH resistant gram-negative bacterial mutants.

In a preferred embodiment, the stress-resistant *Salmonella* used in the methods and compositions of the invention are attenuated. Preferably, the attenuated stress-resistant *Salmonella* mutants used in the methods and compositions of the invention have one or more mutations in one or more genes which reduce the virulence and toxicity of *Salmonella*. In a preferred embodiment, the attenuated stress-resistant *Salmonella* used in the compositions and methods of the invention have mutation(s) in one or more genes in the lipopolysaccharide (LPS) biosynthetic pathway (preferably in the msbB gene) and optionally, have one or more mutations to auxotrophy for one or more nutrients or metabolites, such as uracil biosynthesis, purine biosynthesis, tyrosine biosynthesis, leucine, isoleucine biosynthesis, arginine biosynthesis, valine biosynthesis, tryptophan biosynthesis and arginine biosynthesis.

The growth of an attenuated stress-resistant *Salmonella* used in accordance with the invention may be sensitive to a chelating agent such as, e.g., Ethylenediaminetetraacetic Acid (EDTA), Ethylene Glycol-bis($\beta$-aminoethyl Ether) N,N,N',N'-Tetraacetic Acid (EGTA), or sodium citrate. For example, a chelating agent may inhibit the growth of an attenuated *Salmonella* for viral infection prophylaxis or treatment by about 90%, 95%, 99%, or 99.5% compared to the growth of a wild-type *Salmonella* used in accordance with the invention survive in macrophages at about 50% to about 30%, about 0% to about 10%, or about 10% to about 1% of the level of survival of a wild-type *Salmonella* sp.

The present invention provides a mutant *Salmonella* sp. for viral infection prophylaxis or treatment comprising a genetically modified msbB gene and a mutation characterized by increased growth when grown under $CO_2$ conditions compared to the msbB– mutant *Salmonella* designated YS1646 having ATCC Accession No. 202165. The present invention also provides a mutant *Salmonella* sp. for viral infection prophylaxis or treatment comprising a genetically modified msbB gene and a mutation characterized by increased growth when grown in acidified media compared to the msbB⁻ mutant *Salmonella* designed YS1646 having ATCC Accession No. 202165. The present invention further provides a mutant *Salmonella* sp. for viral infection prophylaxis or treatment comprising a genetically modified msbB gene and a mutation characterized by increased growth in media with high osmolarity compared to the msbB⁻ mutant *Salmonella* designed YS1646 having ATCC Accession No. 202165. Such mutant *Salmonella* sp. may further comprise one or more genetically modified genes to auxotrophy. In a preferred embodiment, the present invention provides *Salmonella* mutants comprising a genetically modified msbB gene and a genetically modified zwf gene.

6.1.1. Characteristics of $CO_2$—Resistant Gram-Negative Bacterial Mutant

The primary characteristic of $CO_2$-resistant gram-negative bacterial mutants is the enhanced percentage of their recovery on LB agar in $CO_2$ relative to the parental strain of bacteria from which they were derived. In one embodiment, the percent recovery of $CO_2$-resistant gram-negative mutants grown under $CO_2$ conditions is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the recovery of the parental strain of bacteria from which the $CO_2$-resistant gram-negative bacterial mutants were derived grown under the same conditions.

A secondary characteristic of $CO_2$-resistant gram-negative bacterial mutants with mutations in lipid biosynthesis genes that suppress TNF-α induction is that the derived mutant retain the same low-level induction of TNF-α. In one embodiment, the percent TNF-α induction is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of the wild type strain of bacteria grown under the same conditions.

As the pH tends to drop during incubation in 5% $CO_2$, some $CO_2$-resistant gram-negative mutants may have increased growth in acidified media relative to the parental strain of bacteria from which they were derived. Thus, $CO_2$-resistant clones may be tested for resistance to acidic pH (such as pH 6.7 or lower), utilizing the methods described infra. In one embodiment, $CO_2$-resistant gram-negative mutants grow approximately 2% to approximately 95%, approximately 2% to approximately 75%, approximately 2% to approximately 50%, approximately 2% to approximately 40%, approximately 2% to approximately 30%, approximately 2% to approximately 25%, or approximately 2% to approximately 10% less in acidified media than the parental strains of bacteria from the $CO_2$-resistant gram-negative mutants were derived.

In addition, some $CO_2$-resistant gram-negative mutants may be more attenuated than the parental strains of bacteria from which they were derived.

6.1.2. Characteristics of Acid pH-Resistant Gram-Negative Bacterial Mutants

The primary characteristic of acid pH-resistant gram-negative bacterial mutants is their ability to grow in liquid media under acidic pH conditions (e.g., pH 6.7, ph 6.6, pH 6.5, pH 6.25, pH 6.0, pH 5.5, pH 5.0, pH 4.5, pH 4.0, pH 3.5, pH 3.0, pH 2.5, pH 2.0, pH 1.5, pH 1.0 or lower) relative to the parental strain of bacteria from which they were derived. In one embodiment, the growth of the acid pH-resistant gram-negative mutants in acidified media is approximately 2% to approximately 95%, approximately 2% to approximately 75%, approximately 2% to approximately 50%, approximately 2% to approximately 40%, approximately 2% to approximately 30%, approximately 2% to approximately 20% or approximately 2% to approximately 10% or higher than the growth of the parental strain of bacteria from which the acid pH-resistant gram-negative bacterial mutants were derived grown under the same conditions. In a preferred embodiment, the growth of the acid pH-resistant gram-negative mutants in acidified media is approximately 40% to 100% higher than the growth of the parental strain of bacteria from which the acid pH-resistant gram-negative bacterial mutants were derived grown under the same conditions.

A secondary characteristic of acidic pH-resistant gram-negative bacterial mutants with mutations in lipid biosynthesis genes that suppress TNF-α induction is that the derived mutant retain the same low-level induction of TNF-α. In one embodiment, the percent TNF-α induction is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of the wild type strain of bacteria grown under the same conditions.

Some acid pH-resistant gram-negative mutants under $CO_2$ conditions may have enhanced recovery relative to the parental strain of bacteria from which they were derived under the same conditions. Thus, acid pH-resistant clones may be tested for enhanced recovery under $CO_2$ conditions, utilizing the methods described herein.

Some acid pH-resistant gram-negative mutants may have increased sensitivity to osmolarity. In addition, some acid pH-resistant gram-negative mutants may be more attenuated than the parental strains of bacteria from which they were derived.

6.1.3. Characteristics of Osmolarity-Resistant Gram-Negative Bacterial Mutants

The primary characteristic of osmolarity-resistant gram-negative bacterial mutants is their ability to survive and/or grow in media having high osmolarity relative to the parental strain of bacteria from which they were derived. In one embodiment, the survival and/or growth of the osmolarity-resistant gram-negative bacterial mutants in media having high osmolarity is approximately 2% to approximately 95%, approximately 2% to approximately 75%, approximately 2% to approximately 50%, approximately 2% to approximately 40%, approximately 2% to approximately 30%, approximately 2% to approximately 25%, approximately 2% to approximately 20% or approximately 2% to approximately 10% better than the survival and/or growth of the parental strain of bacteria from which the osmolarity-resistant gram-negative bacterial mutants were derived grown under the same conditions. In a preferred embodiment, the survival and/or growth of the osmolarity-resistant gram-negative bacterial mutants in media having high osmolarity is approximately 40% to 100% better than the survival and/or growth of the parental strain of bacteria from which the osmolarity-resistant gram-negative bacterial mutants were derived grown under the same conditions.

A secondary characteristic of osmolarity-resistant gram-negative bacterial mutants with mutations in lipid biosynthesis genes that suppress TNF-α induction is that the derived mutant retain the same low-level induction of TNF-α. In one embodiment, the percent TNF-α induction is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of the wild type strain of bacteria grown under the same conditions.

Some osmolarity-resistant gram-negative bacterial mutants may have increased sensitivity to $CO_2$ and/or acid pH stress conditions relative to the parental strains of bacteria from which they were derived. Further, some osmolarity-resistant gram-negative bacterial mutants may have increased sensitivity to $CO_2$ and/or acid pH stress conditions relative to the parental strains of bacteria from which they were derived, but the sensitivity of the osmolarity-resistant gram-negative bacterial mutants to $CO_2$ and/or acid pH stress conditions is compensated for by other genetic alterations (e.g., alterations which cause resistance to $CO_2$ and/or acid pH stress conditions).

In addition, some osmolarity-resistant gram-negative bacterial mutants may be more attenuated than the parental strains of bacteria from which they were derived.

6.2. Production of Stress-Resistant Gram-Negative Bacterial Mutants

Genetic alterations that confer resistance to one or more environmental stresses to gram-negative bacteria, preferably attenuated gram-negative bacteria and more preferably attenuated gram-negative bacteria for viral infection prophylaxis or treatment, can be produced utilizing any method well-known to one of skill in the art. For example, stress-resistant gram-negative bacterial mutants may be obtained by growing the bacteria under various selective pressures or by random mutagenesis (e.g., using a transposon library, using a multicopy plasmid library or by exposing the bacteria to various mutagens). Examples of growth condition parameters which may be varied to obtain stress-resistant mutants include, but are not limited to, the temperature, the type of media used to grow the bacteria, the pH of the media, and the $CO_2$ concentration/levels. Examples of mutagens which may be used to obtain stress-resistant mutants include, but are not limited to, ultraviolet light and nitrosoguanadine.

6.3 Identification and Selection of Stress-Resistant Gram-Negative Bacterial Mutants Gram-negative bacteria, preferably attenuated gram-negative bacteria, and/or preferably attenuated gram-negative bacteria for viral infection prophylaxis or treatment, with resistance to one or more environmental stresses can be identified and selected for utilizing any method well-known to one of skill in the art. In general, a pool of bacteria with genetic variations is subjected to one or more selection criteria and the resistant clones are isolated. A pool of gram-negative bacteria with genetic variations may be composed of spontaneous mutants, a library of transposon mutants or mutants transformed with a library of cloned DNA in a multicopy plasmid. The selected techniques that a pool of gram-negative bacteria with genetic variations is subjected to varies depending upon the particular stress-resistant mutant that one is attempting to select. Selection techniques for a particular stress-resistant gram-negative bacteria may include, e.g., plating the bacteria to LB agar plates under the stress condition, growing the bacteria in LB broth under the stress condition, and then plating the bacteria to LB agar plates. Individual colonies are then isolated from the agar plates and tested for growth under the particular stress condition. Colonies with greater growth ability than the parental strain of bacteria from which they were derived are deemed to be resistant to the particular stress condition. In a specific embodiment, individual colonies of gram-negative bacteria with genetic variations are deemed to be resistant to a particular stress condition if they grow 2 fold, preferably 4 fold, 6 fold, 8 fold, 10 fold, 15 fold, 20 fold, 25 fold, 30 fold, 35 fold, 45 fold, 50 fold, 55 fold, 60 fold, 65 fold, 70 fold, 75 fold or higher levels under the stress condition than the parental strain of bacteria from which they were derived. In another embodiment, individual colonies of gram-negative bacteria with genetic variations are deemed to have resistance to a particular stress condition if their growth is 5%, preferably 10%, 15%, 20%, 25%, 30%, 35%, 40%, 45%, 50%, 55%, 60%, 65%, 70%, 75%, 80%, 85%, 90%, 95% or greater under stress conditions than the parental strain of bacteria from which they were derived.

In order to distinguish spontaneous stress-resistant mutants from transposon and plasmid-based clones, the transposon or plasmid can be transferred to another strain using selection for the appropriate antibiotic marker found on the transposon or plasmid. Several sibling colonies may then be isolated and tested for resistance to the particular stress condition, thus avoiding spontaneous mutants. In order to simultaneously transfer large numbers of transposon or plasmid-based stress-resistant clones to distinguish them from spontaneous stress-resistant clones, following the first selection where the bacteria are grown under stress conditions, the clones may be pooled together, the genetic marker transferred, and then multiple sibling clones tested for growth under the stress condition.

6.3.1. Identification and Selection of $CO_2$—Resistant Gram-Negative Bacterial Mutants Gram-negative bacteria, preferably attenuated gram-negative bacteria, with resistance to $CO_2$ can be identified and selected for utilizing any method well-known to one of skill in the art. In general, a pool of bacteria with genetic variations is subjected to one or more selection criteria and the resistant clones are isolated. A pool of gram-negative bacteria with genetic variations may be composed of spontaneous mutants, a library of transposon mutants or mutants transformed with a library of cloned DNA in a multicopy plasmid. Selection techniques for isolating $CO_2$-resistant gram-negative bacteria may include, but are not limited to, growing the bacteria on LB agar plates at 37° C. under $CO_2$ conditions, growing the bacteria in LB broth at 37° C. in $CO_2$, and then growing the bacteria on LB agar plates at 37° C. under $CO_2$ conditions or air. Individual colonies are then isolated from the agar plates and tested for plating efficiency on LB agar at 37° C. in air and LB agar at 37° C. in $CO_2$. Colonies with greater than 0.5%, preferably 1%, 2%, 5%, 10%, 15%, 20%, 25%, 30%, 35%, 40%, 45%, or 50% recover on the LB agar at 37° C. in $CO_2$ are deemed to have enhanced resistance to $CO_2$ relative to the parental strain of bacteria from which they were derived.

In order to distinguish spontaneous $CO_2$-resistant mutants from transposon and plasmid-based clones, the transposon or plasmid can be transferred to another strain using selection for the appropriate antibiotic marker found on the transposon or plasmid. Several sibling colonies may then be isolated and tested for resistance to $CO_2$, thus avoiding spontaneous mutants. In order to simultaneously transfer large numbers of transposon or plasmid-based stress-resistant clones to distinguish them from spontaneous $CO_2$-resistant clones, following the first selection where the bacteria are grown on LB agar plates under $CO_2$ conditions, the clones may be pooled together, the genetic marker transferred, and then multiple sibling clones tested for growth under the $CO_2$ conditions.

6.3.2. Identification and Selection of Acid pH-Resistant Gram-Negative Bacterial Mutants Gram-negative bacteria, preferably attenuated gram-negative bacteria, with resistance to acidic pH can be identified and selected for utilizing any method well-known to one of skill in the art. In general a pool of bacteria with genetic variations is subjected to one or more selection criteria and the resistant clones are isolated. A pool of gram-negative bacteria with genetic variations may be composed of spontaneous mutants, a library of transposon mutants or mutants transformed with a library of cloned DNA in a multicopy plasmid. Selection techniques for isolating acid pH-resistant gram-negative bacteria may include, but are not limited to, plating the bacteria on LB agar plates at 37° C. at an acidic pH (e.g., pH 6.7, pH 6.6, pH 6.5, pH 6.4, pH 6.0, pH 5.5, pH 5.0, pH 4.5, pH 4.0, pH 3.5, pH 2.0, pH 2.5 or pH 1.0), growing the bacteria in LB broth at 37° C. at an acidic pH (e.g., pH 6.7, pH 6.6, pH 6.5, pH 6.4, pH 6.0, pH 5.5, pH 5.0, pH 4.5, pH 4.0, pH 3.5, pH 2.0, pH 2.5 or pH 1.0), and then plating the bacteria on LB agar plates at 37° C. Individual colonies are then isolated from the agar plates and tested for growth in acidified media at 37° C. Colonies with greater growth ability than the parental strain of bacteria from which they were derived are deemed to be resistant to a particular acid pH (e.g., pH 6.5, pH 6, pH 5, pH 4.5, pH 4, pH 3.5, pH 2, pH 2.5 or pH 1). In a specific embodiment, individual colonies of gram-negative bacteria with genetic variations are deemed to be resistant to an acidic pH (e.g., pH 6.5, pH 6, pH 5, pH 4.5, pH 4, pH 3.5, pH 2, pH 2.5 or pH 1) if they grow 2 fold, preferably 4 fold, 6 fold, 8 fold, 10 fold, 15 fold, 20 fold, 25 fold, 30 fold, 35 fold, 45 fold, 50 fold, 55 fold, 60 fold, 65 fold, 70 fold, 75 fold or higher levels in acidified media than the parental strain of bacteria from which they were derived. In another embodiment, individual colonies of gram-negative bacteria with genetic variations are deemed to have resistance to an acidic pH if their growth is 5%, preferably 10%, 15%, 20%, 25%, 30%, 35%, 40%, 45%, 50%, 55%, 60%, 65%, 70%, 75%, 80%, 85%, 90%, 95% or greater in acidified media than the parental strain of bacteria from which they were derived.

In order to distinguish spontaneous acid pH-resistant mutants from transposon and plasmid-based clones, the transposon or plasmid can be transferred to another strain using selection for the appropriate antibiotic marker found on the transposon or plasmid. Several sibling colonies may then be isolated and tested for resistance to an acidic pH, thus avoiding spontaneous mutants. In order to simultaneously transfer large numbers of transposon or plasmid-based stress-resistant clones to distinguish them from spontaneous acid pH-resistant clones, following the first selection where the bacteria are grown on LB agar plates at an acidic pH, the clones may be pooled together, the genetic marker transferred, and then multiple sibling clones tested for growth in acidified media.

6.3.3. Identification and Selection of Osmolarity-Resistant Gram-Negative Bacterial Mutants Gram-negative bacteria, preferably attenuated gram-negative bacteria, and more preferably attenuated gram-negative bacteria, with resistance to high osmolarity can be identified and selected for utilizing any method well-known to one of skill in the art. In general, a pool of bacteria with genetic variations is subjected to one or more selection criteria and the resistant clones are isolated. A pool of gram-negative bacteria with genetic variations may be composed of spontaneous mutants, a library of transposon mutants or mutants transformed with a library of cloned DNA in a multicopy plasmid. Selection techniques for isolating high osmolarity-resistant gram-negative bacteria may include, but are not limited to, growing the bacteria on agar plates having high osmolarity at 37° C., growing the bacteria in nutrient broth having high osmolarity at 37° C., and then growing the bacteria on agar plates having or not having high osmolarity at 37° C. Examples of agents that result in high osmolarity include, but are not limited to, salts (e.g., NaCl or KCl) and sugars (e.g., sucrose or glucose). Individual colonies are then isolated from the agar plates and tested for growth in media having high osmolarity at 37° C. Colonies with greater growth ability than the parental strain of bacteria from which they were derived are deemed to have resistance to high osmolarity. In a specific embodiment, individual colonies of gram-negative bacteria with genetic variations are deemed to have resistance to high osmolarity if they grow to 2 fold, preferably 4 fold, 6 fold, 8 fold, 10 fold, 15 fold, 20 fold, 25 fold, 30 fold, 35 fold, 45 fold, 50 fold, 55 fold, 60 fold, 65 fold, 70 fold, 75 fold or higher levels in media having high osmolarity than the parental strain of bacteria from which they were derived. In another embodiment, individual colonies of gram-negative bacteria with genetic variations are deemed to have resistance to high osmolarity if their growth is 5%, preferably 10%, 15%, 20%, 25%, 30%, 35%, 40%, 45%, 50%, 55%, 60%, 65%, 70%, 75%, 80%, 85%, 90%, 95% or greater in media having high osmolarity than the parental strain of bacteria from which they were derived.

In order to distinguish spontaneous osmolarity-resistant mutants from transposon and plasmid-based clones, the transposon or plasmid can be transferred to another strain using selection for the appropriate antibiotic marker found on the transposon or plasmid. Several sibling colonies may then be isolated and tested for resistance to high osmolarity, thus avoid spontaneous mutants. In order to simultaneously transfer large numbers of transposon or plasmid-based stress-resistant clones to distinguish them from spontaneous osmolarity-resistant clones, following the first selection where the bacteria are grown on LB agar plates having high osmolarity, the clones may be pooled together, the genetic marker transferred, and then multiple sibling clones tested for growth in media having high osmolarity.

6.4 Genetic Modifications to Stress-Resistant Mutants with Transposon Insertions Stress-resistant gram-negative mutants with transposon insertions can be re-engineered to have a deletion and/or insertion in the same site in order to eliminate the antibiotic resistance and transposon element. First, the site of the transposon insertion is determined using standard techniques well-known to those skilled in the art. Such techniques include, e.g., cloning from chromosomal DNA based on selection for antibiotic resistance and sequencing of the adjacent region, using GenomeWalker™ (Clontech, Palo Alto, Calif.) or direct chromosomal sequencing (Qiagen, Valencia, Calif.). A deletion and/or insertion is then constructed using PCR to generate the two segments necessary for the use of the sucrase vector (Donnenberg and Kaper, 1991, Infection and Immunity 59: 4310-4317). A multiple cloning site can be engineered at the junction of the two segments used to create an insertion. The insertion can be non-coding DNA or coding DNA (e.g., a nucleotide sequence encoding a therapeutic molecule such as prodrug-converting enzyme).

The genetic modification of a spontaneous mutant may be identified using standard techniques well-known to one of skill in the art. One technique to identify the genetic modification(s) of a spontaneous mutant uses linkage to transposons, as described by Murray et al., 2001, J. Bacteriology 183: 5554-5561. Another technique to identify the genetic modification(s) of a spontaneous mutant is to generate a DNA library derived from the strain of interest in a low-copy or transposon vector and to select for resistance to a particular stress condition. The plasmid or transposon DNA is then sequenced as described above. Another technique to identify the genetic modification(s) of a spontaneous mutant is to use a Genechip approach. In the Genechip approach differences between the spontaneous mutant and the parental strain are identified. The spontaneous deletion, rearrangement, duplication or other form of mutation identified in the spontaneous mutant may then be re-engineered into a multicopy plasmid such as asd vector or a sucrase chromosomal vector as described above.

6.5. Kits

Similarly, the invention may also provide a kit comprising (a) a first container comprising a bacterial expression codon optimized antigen from a pathogenic avian influenza virus strain containing unique genetically engineered restriction sites contained within either a bacterial protein expression plasmid or a bacterial chromosomal protein expression vector and (b) a second container comprising bacterial vector(s) with one or more (e.g., fH1, fH2 or fH0) flagellar antigen(s) and/or various non-overlapping O-antigens. Component (a) will be modifiable to genetically match an emerging avian influenza virus using standard in vitro molecular techniques and can be combined with component (b) to generate one or more bacterial strains with defined flagellar antigens which constitute a live vaccine. The variation(s) in flagellar antigens provided by the kit provide for more than one live vaccine strain in which a first immunization (prime) using one strain may be followed at an appropriate time such as 2 to 4 weeks by a second immunization (boost) using a second strain with a different fH antigen or no fH antigen. The live vaccine compositions are suitable for oral administration to an individual to provide protection from avian influenza.

The invention also provides a pharmaceutical pack or kit comprising one or more containers with one or more of the components of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In a specific embodiment of the invention, the kit comprises one or more stress-resistant gram-negative bacterial mutants and optionally means of administering the pharmaceutical compositions of the invention. The different stress-resistant gram-negative bacterial mutants may comprise nucleotide sequences encoding one or more therapeutic molecules. The kit may further comprise instructions for use of said stress-resistant gram-negative bacterial mutants. In certain embodiments of the invention, the kit comprises a document providing instruction for the use of the composition of the invention in, e.g., written and/or electronic form. Said instructions provide information relating to, e.g., dosage, method of administration, and duration of treatment.

In one embodiment, a kit of the invention comprises a stress-resistant gram-negative bacterial mutant in a vial and instructions for administering the stress-resistant gram-negative bacterial mutants for viral prophylaxis or treatment, wherein the stress-resistant gram-negative bacterial mutant is a facultative anaerobe or facultative aerobe. In accordance with this embodiment, the stress-resistant gram-negative bacterial mutant may be engineered to express one or more nucleic acid molecules encoding one or more therapeutic molecules. In another embodiment, a kit of the invention comprises an anti-viral agent contained in a first vial, a stress-resistant gram-negative bacterial mutant in a second vial, and instructions for administering the anti-viral agent and stress-resistant gram-negative bacterial mutant to a subject for viral infection prophylaxis or treatment. In accordance with this embodiment, stress-resistant gram-negative bacterial mutant may be engineered to express one or more nucleic acid molecules encoding one or more therapeutic molecules. Preferably, the stress-resistant gram-negative bacterial mutants included in the kits of the invention are stress-resistant gram-negative *Salmonella* mutants.

In another embodiment, a kit of the invention comprises an attenuated stress-resistant gram-negative bacterial mutant in a vial and instructions for administering the attenuated stress-resistant gram-negative bacterial mutant to a subject for viral infection prophylaxis or treatment, wherein the attenuated stress-resistant gram-negative bacterial mutant is a facultative anaerobe or facultative aerobe. In accordance with this embodiment, the attenuated stress-resistant gram-negative bacterial mutant may be engineered to express one or more nucleic acid molecules encoding one or more therapeutic molecules. In another embodiment, a kit of the invention comprises an anti-viral agent contained in a first vial, an attenuated stress-resistant gram-negative bacterial mutant contained in a second vial, and instructions for administering the anti-viral agent and attenuated stress-resistant gram-negative bacterial mutant to a subject for viral infection prophylaxis or treatment. In accordance with this embodiment, the attenuated stress-resistant gram-negative bacterial mutant may be engineered to express one or more nucleic acid molecules encoding one or more therapeutic molecules. Preferably, the attenuated stress-resistant gram-negative bacterial mutants included in the kits of the invention are attenuated stress-resistant gram-negative *Salmonella* mutants.

In another embodiment, a kit of the invention comprises a stress-resistant gram-negative bacterial mutant for viral infection prophylaxis or treatment in a vial and instructions for administering the stress-resistant gram-negative bacterial mutant to a subject, where the stress-resistant gram-negative bacterial mutant is a facultative anaerobe or facultative aerobe. In accordance with this embodiment, the stress-resistant gram-negative bacterial mutant may be engineered to express one or more nucleic acid molecules encoding one or more therapeutic molecules. In another embodiment, a kit of the invention comprises an anti-viral agent contained in a first vial, a stress-resistant gram-negative bacterial mutant contained in a second vial, and instructions for administering the anti-viral agent and stress-resistant gram-negative bacterial mutant to a subject with a for viral infection prophylaxis or treatment. In accordance with this embodiment, the stress-resistant gram-negative bacterial mutant may be engineered to express one or more nucleic acid molecules encoding one or more therapeutic molecules.

The present invention incorporates a combination of bacterial vector and protein expression technology which results in a unique vaccine which is rapidly constructed in response to emerging avian influenza and their highly pathogenic derivatives. The present invention is directed to the construction bacterially codon optimized avian and human influenza genes and their incorporation into a *Salmonella* strain for therapeutic use in the prevention of avian influenza and highly pathogenic derivatives. An antigen-expressing plasmid or chromosomal construct in the bacterial strains described herein may also contain one or more transcriptional terminators adjacent to the 3' end of a particular nucleotide sequence on the plasmid to prevent undesired transcription into another region of the plasmid or chromosome. Such transcription terminators thus serve to prevent transcription from extending into and potentially interfering with other critical plasmid functions, e.g., replication or gene expression. Examples of transcriptional terminators that may be used in the antigen-expressing plasmids described herein include, but are not limited to, the TI and T2 transcription terminators from 5S ribosomal RNA bacterial genes (see, e.g., FIGS. 1-5; Brosius and Holy, Proc. Natl. Acad. Sci. USA, 81: 6929-6933 (1984); Brosius, Gene, 27(2): 161-172 (1984); Orosz et al., Eur. J Biochem., 20(3): 653-659 (1991)).

The mutations in an attenuated bacterial host strain may be generated by integrating a homologous recombination construct into the chromosome or the endogenous *Salmonella* virulence plasmid (Donnenberg and Kaper, 1991; Low et al. (Methods in Molecular Medicine, 2003)). In this system, a suicide plasmid is selected for integration into the chromosome by a first homologous recombination event, followed by a second homologous recombination event which results in stable integration into the chromosome. The antigen-expressing chromosomal integration constructs described herein comprise one or more nucleotide sequences that encode one or more polypeptides that, in turn, comprise one or more avian influenza antigens, such as the hemagglutinin and neuraminidase polypeptide antigens, or immunogenic portions thereof, from avian influenza virus and highly pathogenic derivatives. Such coding sequences are operably linked to a promoter of transcription that functions in a *Salmonella* bacterial strain even when such a bacterial strain is ingested, i.e., when a live vaccine composition described herein is administered orally to an individual. A variety of naturally occurring, recombinant, and semi-synthetic promoters are known to function in enteric bacteria, such as *Escherichia coli* and serovars of *S. enterica* (see, e.g., Dunstan et al., Infect. Immun., 67(10): 5133-5141 (1999)). Promoters (P) that are useful in the invention include, but are not limited to, well known and widely used promoters for gene expression such as the naturally occurring Plac of the lac operon and the semi-synthetic Ptrc (see, e.g., Amman et al., Gene, 25 (2-3): 167-178 (1983)) and Ptac (see, e.g., Aniann et al., Gene, 69(2): 301-315 (1988)), as well as PpagC (see, e.g., Hohmann et al., Proc. Natl. Acad. Sci. USA, 92. 2904-2908 (1995)), PpmrH (see, e.g., Gunn et al., Infect. Immun., 68: 6139-6146 (2000)), PpmrD (see, e.g., Roland et al., J Bacteriol., 176: 3589-3597 (1994)), PompC (see, e.g., Bullifent et al., Vaccine, 18: 2668-2676 (2000)), PnirB (see, e.g., Chatfield et al., Biotech. (NY), 10: 888-892 (1992)), PssrA (see, e.g., Lee et al., J Bacteriol. 182. 771-781 (2000)), PproU (see, e.g., Rajkumari and Gowrishankar, J Bacteriol., 183. 6543-6550 (2001)), Pdps (see, e.g., Marshall et al., Vaccine, 18: 1298-1306 (2000)), and PssaG (see, e.g., McKelvie et al., Vaccine, 22: 3243-3255 (2004)), Some promoters are known to be regulated promoters that require the presence of some kind of activator or inducer molecule in order to transcribe a coding sequence to which they are operably linked. However, some promoters may be regulated or inducible promoters in *E. coli*, but function as unregulated promoters in *Salmonella*. An example of such a promoter is the well known trc promoter ("Ptrc", see, e.g., Amman et al., Gene, 25(2-3): 167-178 (1983); Pharmacia-Upjohn). As with Plac and Ptac, Ptrc functions as an inducible promoter in *Escherichia coli* (e.g., using the inducer molecule isopropyl-p-D-1 8 thio-galactopyranoside, "IPTG"), however, in *Salmonella* bacteria having no Lad repressor, Ptrc is an efficient constitutive promoter that readily transcribes avian influenza antigen-containing polypeptide coding sequences present on antigen-expressing plasmids described herein. Accordingly, such a constitutive promoter does not depend on the presence of an activator or inducer molecule to express an antigen-containing polypeptide in a strain of *Salmonella*.

The avian influenza antigen-expressing chromosomal integration constructs which integrate into the live vaccine strains also contain an origin of replication (ori) that enables the precursor plasmids to be maintained as multiple copies in certain the bacterial cells which carry the lambda pir element. For the process of cloning DNA, a number of multi-copy plasmids that replicate in *Salmonella* bacteria are known in the art, as are various origins of replications for maintaining multiple copies of plasmids. Preferred origins of replications for use in the multi-copy antigen-expressing plasmids described herein include the origin of replication from the multi-copy plasmid pBR322 ("pBR ori"; see, e.g., Maniatis et al., In Molecular Cloning: A Laboratoly Manual (Cold Spring Harbor Laboratory, Cold Spring Harbor, 1982), pp. 479-487; Watson, Gene, 70: 399-403, 1988), the low copy origin of replication from pACYC177, and the origin of replication of pUC plasmids ("pUC ori"), such as found on plasmid pUC 1 8 (see, e.g., Yanish-Perron et al., Gene, 33: 103-119 (1985)). Owing to the high degree of genetic identity and homology, any serovar of *S. enterica* may be used as the bacterial host for a live vaccine composition for avian influenza, provided the necessary attenuating mutations and antigen-expressing plasmids as described herein are also employed. Accordingly, serovars of *S. enterica* that may be used in the invention include those selected from the group consisting of *Salmonella enterica* serovar *Typhimurium* ("*S. typhimurium*"), *Salmonella montevideo, Salmonella enterica* serovar *Typhi* ("*S. typhi*"), *Salmonella enterica* serovar *Paratyphi* B ("*S. paratyphi* B"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorum* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anaturn* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *kunzendorf* ("*S. cholerae kunzendorf*"), and *Salmonella enterica* serovar *minnesota* ("*S. minnesota*").

The vaccine compositions described herein may be administered orally to an individual in any form that permits the *Salmonella* bacterial strain of the composition to remain alive and to persist in the gut for a time sufficient to elicit an immune response to one or more avian influenza antigens of avian influenza virus and highly pathogenic derivatives expressed in the *Salmonella* strain. For example, the live bacterial strains described herein may be administered in relatively simple buffer or saline solutions at physiologically acceptable pH and ion content. By "physiologically acceptable" is meant whatever is compatible with the normal functioning physiology of an individual who is to receive a live vaccine composition described herein. Preferably, bacterial strains described herein are suspended in otherwise sterile solutions of bicarbonate buffers, phosphate buffered saline (PBS), or physiological saline, that can be easily swallowed by most individuals. However, "oral" routes of administration may include not only swallowing from the mouth a liquid suspension or solid form comprising a live bacterial strain described herein, but also administration of a suspension of a bacterial strain through a nasal spray or pulmonary inhaler, a nasojejunal or gastrostomy tube, and rectal administration, e.g., by using a suppository comprising a live bacterial strain described herein to establish an infection by such bacterial strain in the lower intestinal tract of the alimentary canal. Accordingly, any of a variety of alternative modes and means may be employed to administer a vaccine composition described herein to the alimentary canal of an individual if the individual cannot swallow from the mouth.

7. FIGURES

Figure 1:
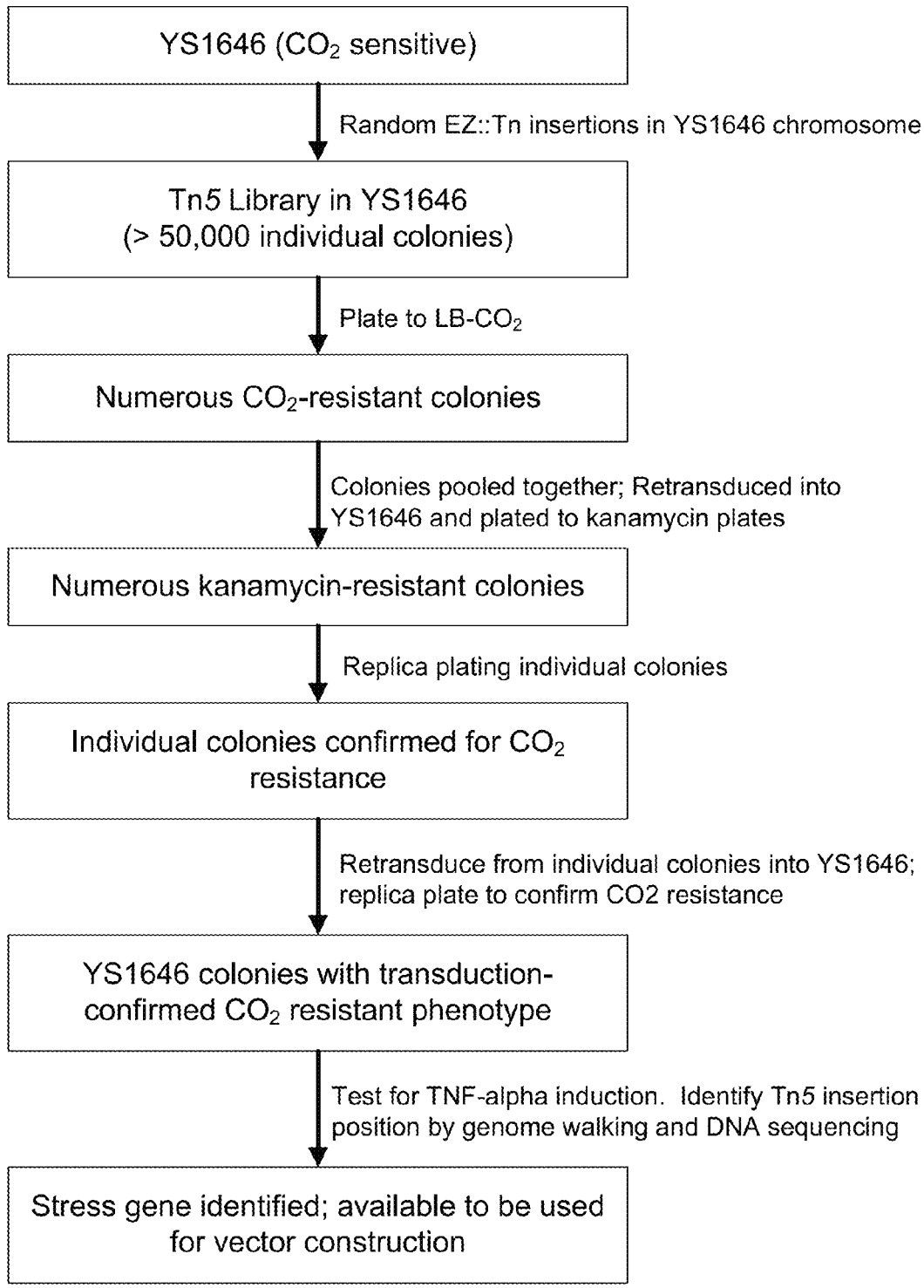
FIG. 1 shows a flow chart depicting the selection scheme for isolation of transposon insertions used to isolate $CO_2$-resistant mutants.

FIG. 1. Selection scheme for isolation of transposon insertions which confer $CO_2$ resistance. Beginning with the YS1646 strain which is $CO_2$ sensitive, a library of mutants is created using transposon insertional mutagenesis (e.g., EZ:: Tn, Epicentre, Madison, Wis.). The library is then plated to LB plates and incubated in a 5% $CO_2$ containing environment at 37° C. This results in numerous colonies on the plates which are $CO_2$ resistant, which could be either due to the transposon, or due to spontaneous mutations. In order to isolate the transposon-related $CO_2$-resistant colonies, the colonies are scraped off the plate using media and a bent glass rod in order to pool the colonies. A phage lysate is prepared from the pooled colonies and used to re-transduce YS1646 which is plated to kanamycin. This results in numerous kanamycin-resistant colonies. These colonies are then individually patched to a master plate and replica plated to LB and incubated in a $CO_2$ environment in order to confirm transponderived $CO_2$ resistance phenotype. The retransduction and replica plating is then performed on an individual colony basis. Colonies confirmed to have $CO_2$ resistance associated with the transposon are subjected to genome walking techniques which results in identifying the chromosomal insertion site.

Figure 2A:
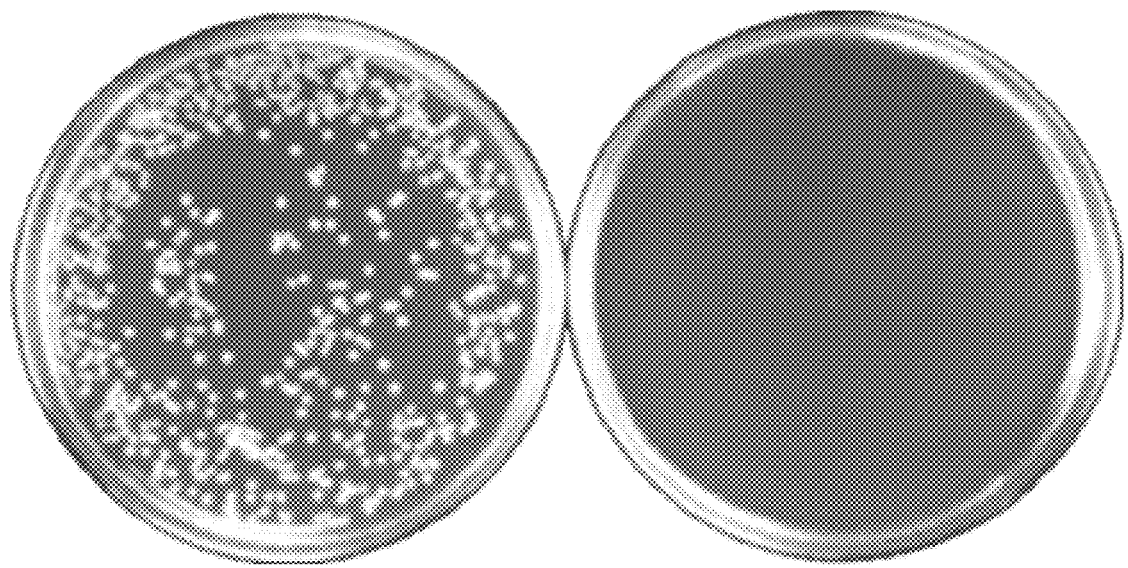
FIG. 2A shows $CO_2$-sensitivity of an msbB− strain derived from *Salmonella* ATCC 14028.
Figure 2B:
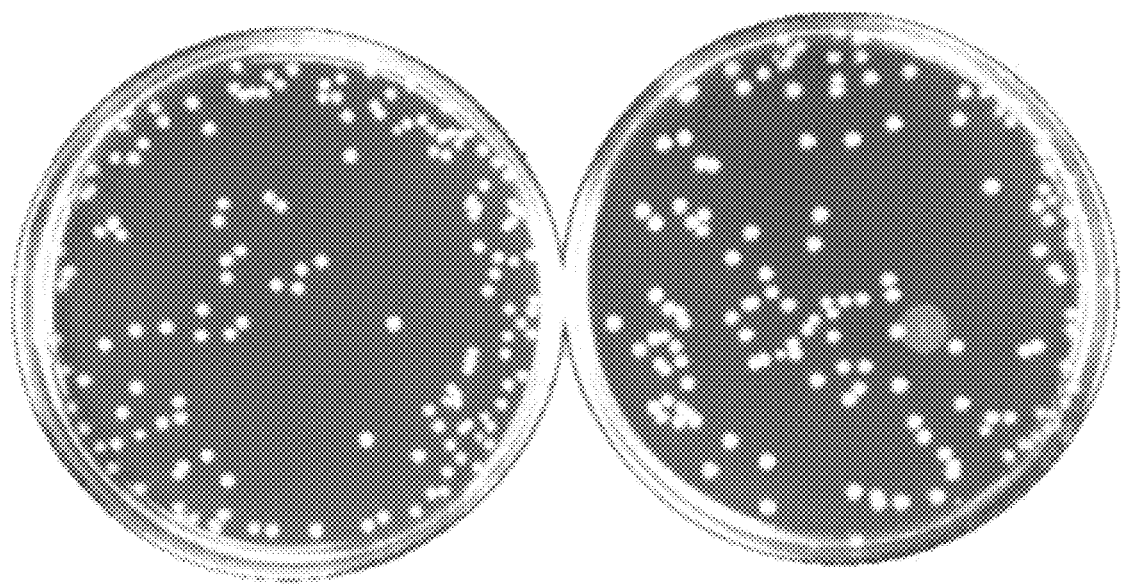
FIG. 2B shows $CO_2$-resistance of a zwf, msbB− strain, each derived from *Salmonella* ATCC 14028.

FIG. 2. Sensitivity and resistance to $CO_2$ shown by comparing colony forming units (CFUs). In each of the two panels, the number of colonies on the right is compared with the number of colonies on the left to indicate sensitivity or resistance. Wild type *Salmonella* on LB media in either air (left) or 5% $CO_2$ showed no sensitivity to the $CO_2$ conditions (not shown in FIGS. 2A and 2B). FIG. 2A shows growth of VNP20009 (YS1646; 41.2.9) on LB media in either air (left) or $CO_2$ (right) showing strong sensitivity to $CO_2$. FIG. 2B shows VNP20009 $\Delta$zwf on LB media in either air (left) or $CO_2$ (right) showing that $\Delta$zwf confers resistance to $CO_2$ of an msbB⁻ strain.

FIG. 3. msbB⁻ confers growth sensitivity in liquid media under $CO_2$ conditions containing physiological amounts of salt and is suppressed by zwf⁻. Two sets of *Salmonella* strains, YS873 and YS873 zwf⁻, and ATCC 14028 and ATCC 14028 zwf⁻ were grown on either LB or LB-0 in either air or $CO_2$. In LB media under ambient air conditions, YS873 and YS873 zwf⁻ show a normal growth curve. However, under $CO_2$ conditions, the YS873 strain is highly inhibited and shows as reduction in the number of CFUs whereas the YS873 zwf⁻ strain grows at a much greater rate. B) In LB-0, the $CO_2$ sensitivity is much less, and is not suppressed by the zwf mutation. C) & D), Wild type *Salmonella* strain ATCC 14028 and 14028 zwf⁻ show similar growth properties in either LB or LB-0 with or without $CO_2$.

Figure 4:
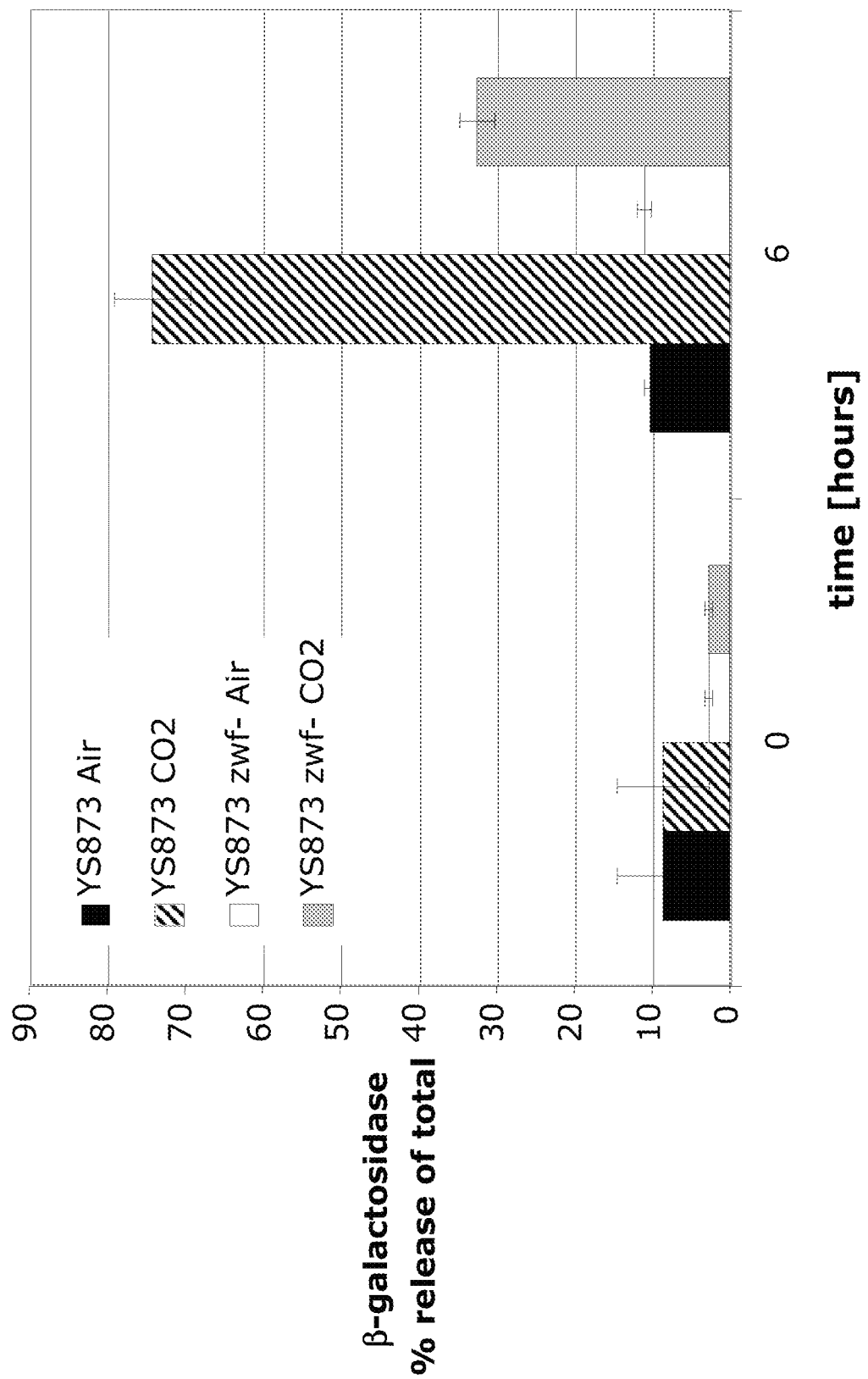
FIG. 4 shows a β-galactosidase release assays confirm cell lysis of msbB− *Salmonella* in LB in the presence of 5% $CO_2$ and that zwf confers resistance.

FIG. 4. β-galactosidase release assays confirm cell lysis in LB in the presence of 5% $CO_2$ and that zwf confers resistance. Release of β-galactosidase from the cytosol of the bacteria was used to test if the decrease in CFU observed in YS873 in LB in the presence of 5% $CO_2$ resulted from cell lysis. The strains used were *Salmonella* YS873 and YS873 zwf⁻ grown under either ambient air or 5% $CO_2$ conditions. After 2 hours growth, there is little difference between the strains under either of the growth conditions. After 6 hours of growth, significant cell lysis, as measured by the release of the cytoplasmic enzyme β-galactosidase, is observed in YS873 grown in the presence of 5% $CO_2$. Furthermore, a loss-of-function mutation in zwf significantly reduces cell lysis in YS873. No significant cell lysis is observed in the absence of $CO_2$.

FIG. 5. zwf suppresses sensitivity to acidic pH in LB broth. Two sets of *Salmonella* strains, YS873 and YS873 zwf⁻, and ATCC 14028 and ATCC 14028 zwf⁻ were grown on LB at either low pH (pH 6.6) or physiological pH (pH 7.6) in either air or 5% $CO_2$. A) Under ambient air conditions, YS873 is strongly growth inhibited at pH 6.6, compared to the YS873 zwf⁻ which suppresses the inhibition and restores normal growth, while at pH 7.6, both strains grow normally. B) Under 5% $CO_2$, the zwf mutation suppressed the sensitivity to acid pH compared to the YS873 strain, which lost viability during the 6 hour time period. Moreover, the zwf mutation changed the pH optimum of the strain, which now grew better at pH 6.6 than at pH 7.6. C) & D), Wild type *Salmonella* strain ATCC 14028 and 14028 zwf⁻ show similar growth properties an either pH 6.6 or pH 7.6 with or without $CO_2$.

FIG. 6. β-galactosidase assays confirm cell lysis in LB broth, pH 6.6 and that zwf⁻ confers resistance. Release of β-galactosidase from the cytosol of the bacteria was used to test if the decrease in CFU observed in YS873 in LB at pH 6.6+/− the presence of 5% $CO_2$ resulted from cell lysis. The strains used were *Salmonella* YS873 and YS873 zwf⁻ grown in LB broth at either pH 6.5 or pH 7.5 under either ambient air or 5% $CO_2$ conditions. A) Under ambient air conditions after 8 hours, significant cell lysis occurs after growth of YS873 in LB broth, pH 6.5 but not pH 7.5. Furthermore, a loss-of-function mutation in zwf significantly reduces cell lysis of YS873 grown in LB broth pH 6.6. B) Under 5% $CO_2$ conditions after 8 hours, cell lysis is suppressed only in the YS873 zwf⁻ strain at pH 6.5, again showing a shift in pH optimum for this strain.

FIG. 7. zwf mutation suppresses both msbB-induced $CO_2$ sensitivity and osmotic defects. Different media and growth conditions were used to indicate the ability of small patches of bacteria (3 each) to grow using the replica plating technique. The strains used are listed on the left: wt, wild type *Salmonella typhimurium* ATCC 14028; YS1, *Salmonella typhimurium* ATCC 14028 containing the msbB mutation; YS1 zwf::kan, the YS1 strain with a kanamycin containing transposing insertion into the zwf gene; YS873, the YS1 strain with a deletion in the somA gene; YS873 zwf::kan, the YS873 strain with a kanamycin containing Tn5 transposon disrupting the zwf gene. Growth conditions maintained at 37° C. used included: A, LB media in air; B, LB media in 5% $CO_2$; C, msbB media; D, msbB media in 5% $CO_2$; E, LB-0 media in air; F, LB-0 media in 5% $CO_2$; G, LB-0 media containing sucrose (total 455 milliosmoles); H, LB-0 media containing sucrose and 5% $CO_2$; I, LB-0+gluconate (glucon.) in air; J, LB-0+gluconate in 5% $CO_2$.

FIG. 8. Selection scheme for isolation of transposon insertions which confer acidic pH resistance. Beginning with the YS1646 strain which is acidic pH sensitive, a library of mutants is created using transposon insertional mutagenesis (e.g., EZ::Tn, Epicentre, Madison, Wis.). The library is then plated to LB plates at pH≤6.6. This results in numerous colonies on the plates which are acidic pH resistant, which could be either due to the transposon, or due to spontaneous mutations. In order to isolate the transposon-related acidic-resistant colonies, the colonies are scraped off the plate using media and a bent glass rod in order to pool the colonies. A phage lysate is prepared from the pooled colonies and used to re-transduce YS1646 which is plated to kanamycin. This results in numerous kanamycin-resistant colonies. These colonies are then individually patched to a master plate and replica plated to LB at pH≤6.6 and incubated in order to confirm transposon-derived acidic pH resistance phenotype. The retransduction and replica plating is then performed on an individual colony basis. Colonies confirmed to have an acidic pH resistant phenotype associated with the transposon are subjected to genome walking techniques which results in identifying the chromosomal insertion site.

FIG. 9. Selection scheme for isolation of transposon insertions which confer osmolarity resistance. Beginning with the YS1646 strain which is osmolarity sensitive, a library of mutants is created using transposon insertional mutagenesis (e.g., EZ::Tn, Epicentre, Madison, Wis.). The library is then plated to LB plates (containing salt). This results in numerous colonies on the plates which are osmolarity resistant, which could be either due to the transposon, or due to spontaneous mutations. In order to isolate the transposon-related osmolarity-resistant colonies, the colonies are scraped off the plate using media and a bent glass rod in order to pool the colonies. A phage lysate is prepared from the pooled colonies and used to re-transduce YS1646 which is plated to kanamycin. This results in numerous kanamycin-resistant colonies. These colonies are then individually patched to a master plate and replica plated to LB and incubated in order to confirm transpon-derived osmolarity resistance phenotype. The retransduction and replica plating is then performed on an individual colony basis. Colonies confirmed to have an osmolarity resistant phenotype associated with the transposon are subjected to genome walking techniques which results in identifying the chromosomal insertion site.

In order to more fully illustrate the invention, the following non-limiting examples are provided.

8. EXAMPLE

Isolation and Identification of a Gene Involved in Resistance to $CO_2$, Acidic pH and/or Osmolarity

8.1. Example

Isolation of $CO_2$ Resistant Strains Using Transposon Libraries

Throughout the procedures, msbB strains were grown in Luria-Bertani (LB) broth containing 10 g tryptone, 5 g yeast extract, 10 g NaCl, pH adjusted as indicated using either 1N NaOH or 1N HCl, or LB plates containing 1.5% agar at 37±2° C. msbB⁻ strains were grown in modified LB referred to as MSB media (msbB media), containing 10 g tryptone, 5 g yeast extract 2 mL 1N $CaCl_2$ and 2 mL 1N $MgSO_4$ per liter, adjusted to pH 7.0 to 7.6 using 1N NaOH, or in LB broth or LB plates lacking NaCl, referred to as LB-0. For transductions, LB lacking EGTA was used. For sucrose resolutions, LB lacking NaCl and containing 5% sucrose at 30±2° C. was used. Auxotrophic mutants are determined on minimal media 56 (M56): 0.037 M $KH_2PO_4$, 0.06 M $Na_2HPO_4$, 0.02% $MgSO_4 7H_2O$, 0.2% $(NH_4)_2SO_4$, 0.001% $Ca(NO_3)_2$, 0.00005% $FeSO_4 7H_2O$, with a carbon source (e.g., glucose 0.1 to 0.3%) as sterile-filtered additive, and further supplemented with the appropriate nutrients, 0.1 mg/ml thiamine and 50 mg/ml each of adenine. Solid M56 media is made by preparing separate autoclaved 2× concentrates of the mineral salts and the agar, which are combined after sterilization. Media are also supplemented with antibiotics used as needed to select for resistance markers, including tetracycline (Sigma) at 4 mg/ml from a stock: 10 mg/ml in 70% ethanol stored in darkness at −20° C. or ampicillin at 100 mg/ml from a stock: 100 mg/ml in $H_2O$, sterile filtered and stored at −20° C. The bacteria used are listed in Table 1.

The library was screened by plating dilutions of the library onto MSB agar and incubating them in 5% $CO_2$ at 37° C. overnight. In particular, colonies were tested for $CO_2$ resistance by plating serial dilutions of the library of bacteria onto MSB plates and incubating the plates at 37° C. in either ambient air or in air with 5% $CO_2$. Colonies that were recovered from MSB plates incubated at 37° C. in air with 5% $CO_2$ were deemed resistant to $CO_2$. The resistance of these colonies to $CO_2$ could be due to either the presence of the transposon insertion or to a spontaneous mutants. In order to eliminate any background of spontaneous mutants, the $CO_2$-resistant colonies were pooled, P22 lysates prepared (P22 phage transduction by the method of Davis et al., 1980, Advanced Bacterial Genetics, Cold Spring Harbor Press, Cold Spring Harbor, N.Y.), and the Tn5 insertions transferred to YS1646 and plates for individual colonies in MSB-kanamycin at 37° C. in ambient air. Individuals colonies were then gridded and replica plated to MSB plates and incubated at 37° C. in either ambient air or in air with 5% $CO_2$. Those colonies which tested positive by the replica plating were chosen for further study of retransduction to confirm the phenotype. These clones were also tested to ensure that there was no significant increase in TNF-α induction using standard techniques such as those described by Low et al., 1999. The $CO_2$ resistant clones chosen to undergo further testing include the clones designated 14.2, 32.2 and 37.2.

An example of the $CO_2$ sensitivity and resistance observed using the plating efficiency method is shown in FIG. 2. The percent growth of the bacteria under a stress condition such as $CO_2$ is determined by plating to MSB agar plates and incubated in either air or $CO_2$, and dividing the number of clones on the stress-subjected plate to the number of clones in the non-stress-subjected plate. General observation of the plate is often sufficient to determine sensitivity and resistance. The wild type bacteria do not show any obvious reduction in the number of CFUs observed, whereas the strain YS1646 shows a dramatic reduction in the number of bacteria observed. The

TABLE 1

| Strain | Parental strain | Genotype | Derivation or source |
|---|---|---|---|
| S. enterica serovar Typhimurium 14028 | Wild type | Wild type | ATCC 14028 Manassas, VA |
| 14028 zwf | 14028 | Δzwf | Replacement of zwf gene with Δzwf by homologous recombination |
| YS1646 (VNP20009) | 14028 | ΔmsbB ΔpurI | Low et al., pp 47-59, In: Suicide Gene Therapy: Methods and Protocols, C. Springer (ed), Humana Press, 2003. |
| YS1 | 14028 | msbB1::Ωtet msbB1::Ωtet | Murray et al. 2001, J. Bacteriol. 183: 5554-5561. |
| YS1 zwf | YS1 | zwf:Tn5 (Kan$^R$) msbB1::Ωtet somA | P22 zwf:Tn5 (Kan$^R$)X YS1 → Kan$_{20}^r$ Murray et al. 2001, J. Bacteriol. 183: 5554-5561. |
| YS873 | 14028 | zbj10:Tn10 msbB1::Ωtet somA zbj10:Tn10 zwf:Tn5 | |
| YS873 zwf | YS873 | (Kan$^R$) | P22 zwf:Tn5 (Kan$^R$)X YS873 → Kan$_{20}^r$ |

$CO_2$ resistant mutants were obtained as outlined in FIG. 1. A Tn5 transposome (EZ::TN, Epicentre, Madison, Wis.) was used to directly generate a library in YS1646, plated to MSB agar plates with the appropriate antibiotic (kanamycin for Tn5) and grown overnight at 37° C. in ambient air. The plates were then flooded with MSB broth and the colonies scraped from the plates, pooled and frozen in aliquots at −80° in 15% glycerol.

$CO_2$ resistant mutant 32.2 shows approximately the same number of colonies when grown either under ambient air conditions or 5% $CO_2$, indicating $CO_2$ resistance. The GenomeWalker (Clonetech, Palo Alto, Calif.) kit was used to determine the chromosomal insertion site in clones designated 14.2, 32.2 and 37.2. The Tn5 was determined to be located in the zwf gene in all three clones, two of them (clones 14.2 and 32.2) were located after base pair 1019 and the third (clone 37.2) was located after base pair 1349. Therefore, zwf⁻ confers $CO_2$ resistance in the msbB⁻ strain YS1646.

8.2. Example

Suppression of $CO_2$-Mediated Growth Inhibition by zwf⁻ Mutants

In order to further analyze the effect of the zwf mutation on growth of the msbB⁻ *Salmonella*, growth rates under different conditions were studied. To generate growth curves, 3 ml broth tubes were inoculated with single colonies and grown on a shaker overnight at 37° C. An adequate amount of LB or LB-0 broth was then inoculated 1:1000 with cells. Cells were held on ice until all inoculations were completed. Triplicate 3 ml aliquots were then placed in a 37° C. shaker with 250 rpm in air or 5% $CO_2$. $O.D._{600}$ was measured every 60 minutes and dilutions of bacteria were plated onto MSB or LB agar plates to calculate the number of colony forming units (CFU) per ml.

FIG. 3 shows the growth of wild type ATCC 14028, 14028 zwf⁻, YS873, and YS873 zwf⁻ in LB and LB-0 broth, grown in the presence or absence of 5% $CO_2$. The growth of YS873 (FIG. 3A), but not ATCC 14028 (FIG. 3C) is greatly impaired LB broth in the presence of 5% $CO_2$. A significant decrease in CFU is observed (FIG. 3A), indicating that YS873 cells lose viability in the presence of 5% $CO_2$ in LB broth. When a loss-of-function mutation in zwf is incorporated into YS873, no loss in viability is observed under identical conditions, although there is a longer lag phase of growth and the CFU does not increase at the same rate as in LB broth in the absence of 5% $CO_2$ (FIG. 3A). In LB-0 broth, there are no growth defects in 14028 or 14028 zwf⁻ (FIG. 3D). For YS873 and YS873 zwf⁻, the growth defects in LB-0 in the presence of 5% $CO_2$ are attenuated in comparison to those observed in LB broth. There is no decrease in viability in YS873 in LB-0 in 5% $CO_2$, although there is a decreased growth rate in both YS873 and YS873 zwf⁻ in LB-0 in the presence of $CO_2$ compared to growth in the absence of $CO_2$ (FIG. 3B).

8.3. Example

Suppression of $CO_2$ Mediated Cell Lysis by zwf⁻ Mutants

To test if the decrease in CFU observed in YS873 in LB in the presence of 5% $CO_2$ resulted from cell lysis, release of β-galactosidase (a cytoplasmic enzyme not normally present in the culture supernatant) was determined. For β-galactosidase expression, lacZ was cloned into the high copy vector pSP72 (Promega) and screened for bright blue colonies on LB agar containing 40 μg/m X-gal. β-gal assays were performed according to the instructions for the Galacto-Star™ chemiluminescent reporter gene assay system (Applied Biosystems, Bedford, Mass.). Briefly, 1 ml of bacterial culture expressing β-Gal from pSP72 was pelleted at 13,000×g for 5 min. Supernatants were filtered through a 0.2 mm syringe filter and then assayed immediately or frozen at −80° C. until assayed with no further processing. Cell pellets were quickly freeze-thawed and suspended in 50 ul or 200 ml B-Per™ bacterial cell lysis reagent (Pierce Chemical) containing 10 mg/ml lysozyme (Sigma). Bacteria were allowed to lyse for 10-20 min. at room temperature and then placed on ice. All reagents and samples were allowed to come to room temperature before use. Filtered supernatants and bacterial lysates were diluted as needed in Galacto-Star™ Lysis Solution or assayed directly. β-gal standard curves were made by preparing recombinant β-gal (Sigma, 600 units/mg) to 4.3 mg/ml stock concentration in 1×PBS. The stock was diluted in Lysis Solution to prepare a standard curve of 100 ng/ml-0.05 ng/ml in doubling dilutions. 20 ml of standard or sample was added to each well of a 96-well tissue culture plate. 100 ml of Galacto-Star™ Substrate diluted 1:50 in Reaction Buffer Diluent was added to each well and the plate rotated gently to mix. The plate was incubated for 90 minutes at 25° C. in the dark and then read for 1 second/well in an L-max™ plate luminometer (Molecular Devices). Sample light units/ml were compared to the standard curve and values converted to units β-gal/ml. Percent release of β-gal was determined by dividing units/ml supernatant by total units/ml (units/ml supernatant+units/ml pellet). All samples were assayed in triplicate. As shown in FIG. 4, after 6 hours of growth, significant cell lysis, as measured by the release of the cytoplasmic enzyme β-galactosidase, is observed in YS873 grown in the presence of 5% $CO_2$. No significant cell lysis is observed in the absence of $CO_2$. Furthermore, a loss-of-function mutation in zwf significantly reduces $CO_2$-mediated cell lysis in YS873.

8.4. Example

Suppression of Acidic pH Mediated Growth Inhibition by zwf Mutants

To test if increased or reduced pH would reduce sensitivity to $CO_2$, LB media was buffered to pH 6.6 or 7.6 and cultures were grown in the presence or absence of 5% $CO_2$. As shown in FIG. 5, wild type ATCC 14028 and ATCC 14028 zwf⁻ grow normally under all conditions (FIGS. 5C & 5D). In contrast, the growth of YS873 is significantly impaired when the pH of LB is 6.6 under ambient air conditions, with no significant increase in CFU after 6 hours (FIG. 5A). In contrast, when the pH of LB is 7.6, YS873 grows well (FIG. 5A). A loss-of-function mutation in zwf allows for YS873 to grow well in LB broth at a pH of 6.6 (FIG. 5A). Under 5% $CO_2$, the zwf mutation suppressed the sensitivity to acid pH compared to the YS873 strain (FIG. 5B), which lost viability during the 6 hour time period. Moreover, the zwf mutation changed the pH optimum of the strain, which now grew better at pH 6.6 than at pH 7.6.

8.5. Example

Suppression of Acidic pH Mediated Cell Lysis by zwf Mutants

Release of β-galactosidase from the cytosol of the bacteria was used to test if the decrease in CFU observed in YS873 in LB at pH 6.6+/− the presence of 5% $CO_2$ resulted from cell lysis (FIG. 6). The strains used were *Salmonella* YS873 and YS873 zwf⁻ grown in LB broth at either pH 6.5 or pH 7.5 under either ambient air or 5% $CO_2$ conditions. Under ambient air conditions after 8 hours, significant cell lysis occurs after growth of YS873 in LB broth, pH 6.5 but not pH 7.5 (FIG. 6A). Furthermore, a loss-of-function mutation in zwf significantly reduced cell lysis of YS873 grown in LB broth pH 6.6. Under 5% $CO_2$ conditions after 8 hours, cell lysis is suppressed only in the YS873 zwf⁻ strain at pH 6.5, again showing a shift in pH optimum for this strain (FIG. 6B).

8.6. Example

Determination of Osmolarity and Gluconate Sensitivity Properties of zwf Mutants Phenotypes of strains were determined by replica plating (FIG. 7). Master plates were made on either MSB or LB-0 agar. Plates were supplemented with sucrose (455 mOsmol) instead of NaCl, or 0.33% gluconate, a downstream product in the same pathway as zwf, thus restoring or enhancing the pathway using a metabolic supplement. Replica plating was performed using a double velvet technique. Plates were incubated for 16 hours at 37° C. in either ambient air or 5% $CO_2$. For comparative purposes, the wild type Salmonella ATCC 14028, YS1, YS1 zwf::kan, YS873 and YS873 zwf::kan were used.

As shown in the replica series of Figure. 7, growth of unsuppressed YS1 is inhibited on LB (FIG. 7A) but YS1 grew well on MSB and LB-0 agar (FIGS. 3C and 3D. In contrast, growth of YS1 on MSB and LB-0 agar is completely inhibited when the plates are incubated in the presence of 5% $CO_2$. The introduction of the zwf mutation completely compensates for the phenotype and allows the bacteria to grow under 5% $CO_2$ on all three media (FIGS. 7 B, D, F). When NaCl in LB plates is substituted with sucrose at iso-osmotic concentrations (FIG. 7 G), growth of YS1 is also inhibited, indicating osmo-sensitivity of YS1. Introduction of the zwf mutation improves growth of YS1 on LB and on LB-0 5% sucrose agar, indicating that the zwf mutation can partially compensate for the msbB-induced osmotic growth defect. YS873, which contains the EGTA and salt resistance suppressor mutation somA (Murray et al., 2001), grows well on LB, MSB, LB-0 and LB-0 sucrose agar plates in air, but not when the plates are incubated in 5% $CO_2$. In contrast, the strain YS873 zwf⁻ is able to grow on all plates in $CO_2$, indicating that the zwf mutation can compensate for the growth defect of msbB strains in $CO_2$. YS873 zwf⁻ was not able to grow on LB-0 gluconate in 5% $CO_2$ (FIGS. 7 I+J), confirming the role of the zwf pathway in $CO_2$ sensitivity.

8.7. Example

Isolation and Identification of Genes Involved in Resistance to Acid pH

The Tn5 insertion library described above is screened to identify mutants with resistance to acidity FIG. 8. The library is screened by dilution of the library onto MSB agar or broth buffered to pH 6.6 with 100 mM sodium phosphate buffer and incubating them at 37° C. overnight. Colonies that were recovered from acidified MSB plates incubated at 37° C. in air are deemed acidic pH resistant. The resistance of these colonies could be due to either the presence of the transposon insertion or to spontaneous mutants. In order to eliminate any background of spontaneous mutants, the acidic pH-resistant colonies are pooled, P22 lysates prepared (P22 phage transduction by the method of Davis et al., 1980, Advanced Bacterial Genetics, Cold Spring Harbor Press, Cold Spring Harbor, N.Y.), and the Tn5 insertions transferred to YS1646 and plated for individual colonies in pH 7.4 MSB-kanamycin at 37° C. in ambient air. Individuals colonies were then gridded and replica plated to pH 6.6 and pH 7.4 MSB plates and incubated at 37° C. Those colonies which tested positive by the replica plating are chosen for further study of retransduction to confirm the phenotype. These clones are also tested to ensure that there was no significant increase in TNF-α induction using standard techniques such as those described by Low et al., 1999. The GenomeWalker (Clonetech, Palo Alto, Calif.) kit is used to determine the chromosomal insertion site in the acidic pH-resistant clones.

8.8. Example

Isolation and Identification of Genes Involved in Resistance to Osmolarity

The Tn5 insertion library described above is screened to identify mutants with resistance to osmolarity FIG. 9. The library is screened by dilution of the library onto MSB agar or broth containing sucrose such that it results in greater than 100 mOsmoles, at physiological osmolarity, (approx 300 mOsmole) or greater (e.g., 450 mOsmole) and incubating them at 37° C. overnight. Colonies that were recovered from physiological osmolarity or greater on MSB plates incubated at 37° C. in air are deemed osmolarity resistant. The resistance of these colonies could be due to either the presence of the transposon insertion or to a spontaneous mutants. In order to eliminate any background of spontaneous mutants, the osmolarity-resistant colonies are pooled, P22 lysates prepared (P22 phage transduction by the method of Davis et al., 1980, Advanced Bacterial Genetics, Cold Spring Harbor Press, Cold Spring Harbor, N.Y.), and the Tn5 insertions transferred to YS1646 and plated for individual colonies in MSB-kanamycin at 37° C. in ambient air. Individuals colonies were then gridded and replica plated to MSB and MSB-sucrose plates and incubated at 37° C. Those colonies which tested positive by the replica plating are chosen for further study of retransduction to confirm the phenotype. These clones are also tested to ensure that there was no significant increase in TNF-α induction using standard techniques such as those described by Low et al., 1999. The GenomeWalker (Clonetech, Palo Alto, Calif.) kit is used to determine the chromosomal insertion site in the osmolarity-resistant clones.

9. EXAMPLES OF INCORPORATION OF STRESS RESISTANCE GENES FOR USE IN GENETICALLY STABILIZED AND ISOLATED STRAINS WITH DEFINED FLAGELLAR ANTIGENS AND THEIR USE IN PROTECTION AGAINST AVIAN INFLUENZA AND HIGHLY PATHOGENIC DERIVATIVES 9.1. Example Construction of an Antibiotic-Sensitive Non-Polar Deletion in zwf A non-polar deletion in zwf was generated by constructing a pCVD442 vector capable of deleting the entire zwf coding region by homologous recombination with the Salmonella chromosome (Donnenberg and Kaper, 1991 Infection & Immunity 59:4310-4317; Low et al., 2003, Methods in Molecular Medicine; Suicide Gene Therapy, C. Springer (ed), Humana Press, pp 47-59, expressly incorporated in their entirety herein). Primers for PCR were designed that would generate one product immediately upstream of the 5' ATG start codon and a separate product immediately downstream of the 3' stop codon of the zwf coding region. The two separate products could then be ligated sequentially into the pCVD442 vector. The primers were: zwf-5'-reverse: 5'-GTG TGA GCT CGT GGC TTC GCG CGC CAG CGG CGT TCC AGC-3' (SEQ ID No.:1) (with added SacI) and zwf-5' forward 5'-GTG TGC ATG CGG GGG GCC ATA TAG GCC GGG GAT TTA AAT GTC ATT CTC CTT AGT TAA TCT CCT GG-3' (SEQ ID No.:2) (with added SphI); and zwf-3' reverse 5'-GTG TGC ATG CGG GGT TAA TTA AGG GGG CGG CCG CAT TTG CCA CTC ACT CTT AGG TGG-3' (SEQ ID No.:3) and 3-forward 5'-GTG TGT CGA CCC TCG CGC AGC GGC GCA TCC GGA TGC-3' (SEQ ID No.:4). The primers also generate internal Not1, PacI, SphI, SfiI, and SwaI in order to facilitate cloning of DNA fragments, such as the influenza H5 and N1 antigens into the Δzwf for stable chromosomal integration without antibiotic resistance. This vector is referred to as pCVD442-Δzwf. Presence of the deletion, in $Amp^S$ $Suc^R$ colonies, was detected with PCR using the following primers: zwf-FL-forward: 5'-ATATTACTCCTG-GCGACTGC-3' (SEQ ID No.:5) and zwf-FL-reverse: 5'-CGACAATACGCTGTGTTACG-3' (SEQ ID No.:6).

9.2. Example

Determination of Improved Penetration and Persistence in Gut Tissues

Standard methods are utilized to determine increased penetration and persistence in gut tissues. In all cases, comparison of different dose levels are performed, comparing the parental, $CO_2$, acidic pH, and/or osmolarity sensitive strain with the $CO_2$, acidic pH and/or osmolarity resistant strain(s). 1) Total recovery from gut material. Mice are orally administered the parental strain and the resistant strains at different dose levels. At fixed times between days 1 and 21 (e.g., d. 1, 7, 14 & 21) the mice are euthanized (avoiding $CO_2$ asphyxiation) and their gut collected by dissection. The gut is then homogenized and serial dilutions plated for Salmonella on Salmonella selective media such as SS agar, bismuth sulfite agar, or Hecktoen enteric agar. The number of Salmonella present for the parental and resistant strains at different times and dosing levels can then be compared to demonstrate improved penetration and persistence in the gut. 2) Determination of gut lining-associated Salmonella. Mice are orally administered the parental strain and the resistant strains at different dose levels. At fixed times between days 1 and 21 (e.g., d. 1, 7, 14 & 21) the mice are euthanized (avoiding $CO_2$ asphyxiation) and their gut collected by dissection. The gut is then repeated flushed with a saline solution containing 100 ug/ml of gentamicin, an antibiotic that does not enter cells and will therefore not kill any bacteria that have penetrated the gut mucosal cells. The gut is then washed with saline to remove traces of gentamicin, homogenized and serial dilutions plated for Salmonella on Salmonella selective media such as SS agar, bismuth sulfite agar, or Hecktoen enteric agar. The number of Salmonella present for the parental and resistant strains at different times and dosing levels can then be compared in order to demonstrate improved gut penetration and persistence in the gut at lower doses.

9.3. Example

Determining Immune Response to H5N1-Expressing Bacteria

Live bacterial vaccines for H5N1 influenza prophylaxis or treatment described by Bermudes (WO/2008/03908) are engineered as described above to have an additional mutation in a stress-resistance gene such as zwf. Experimental determination of vaccine activity is known to those skilled in the arts. By way of non-limiting example, determination of an antibody response is demonstrated.

1) Vertebrate animals including mice, birds, dogs, cats, horses, pigs or humans are selected for not having any known current or recent (within 1 year) influenza infection or vaccination. Said animals are pre-bled to determine background binding to, for example, H5 and N1 antigens.

2) The Salmonella expressing H5 and N1 are cultured on LB agar overnight at 37°. Bacteria expressing other H and or N antigens may also be used.

3) The following day the bacteria are transferred to LB broth, adjusted in concentration to $OD_{600}$=0.1 ($\sim 2\times 10^8$ cfu/ml), and subjected to further growth at 37° on a rotator to $OD_{600}$=2.0, and placed on ice, where the concentration corresponds to approx. $4\times 10^9$ cfu/ml.

4) Following growth, centrifuged and resuspended in $\frac{1}{10}$ the original volume in a pharmacologically suitable buffer such as PBS and they are diluted to a concentration of $10^4$ to $10^9$ c.f.u./ml in a pharmacologically suitable buffer on ice, warmed to room temperature and administered orally or intranasally in a volume appropriate for the size of the animal in question, for example 50 μl for a mouse or 10 to 100 ml for a human. The actual dose measured in total cfu is determined by the safe dose as described elsewhere in this application.

5) After 2 weeks, a blood sample is taken for comparison to the pretreatment sample. A booster dose may be given. The booster may be the same as the initial administration, a different species, a different serotype, or a different flagellar antigen (H1 or H2) or no flagellar antigen.

6) After an additional 2 to 4 weeks, an additional blood sample may be taken for further comparison with the pretreatment and 2 week post treatment.

7) A comparison of preimmune and post immune antibody response is preformed by immunoblot or ELISA. A positive response is indicated by a relative numerical value 2× greater then background/preimmune assay.

9.4. Example

Immunization with H5N1 Bacterial Vaccine Strains

Live bacterial vaccines for H5N1 influenza prophylaxis or treatment described by Bermudes (WO/2008/03908) are engineered as described above to have an additional mutation in a stress-resistance gene such as zwf. An experiment to determine if H5N1 strains of Salmonella are capable of providing protection from challenge with the wildtype strain. Ducks are immunized orally with $5\times 10^9$ cfu of bacteria when 4 weeks old, then challenged with the standard challenge model of avian influenza at 6 weeks age.

Birds in Group A are immunized with empty vector. Group B receive Salmonella H5N1. Group C is immunized with Salmonella expressing the Tamiflu resistant neuraminidase mutations. Birds in Group D are not immunized. Each group is further divided into +/− Tamiflu treatment. Results of these experiments can be used to demonstrate the effectiveness of the vaccine on Tamiflu resistant strain, with and without Tamiflu treatment.

9.5. Example

Immunization with a Trimeric Hemagglutinin Antigen

The bacteria described in Example 9.4 "Immunization with H5N1 Bacterial Vaccine Strains" above, are further engineered to contain a trimeric immunogen described by Wei et al. 2008 (J Virology 82: 6200-6208, expressly incorporated by reference in its entirety herein). The antigen is further modified to contain the HlyA C-terminal 60 amino acids in-frame, in order to guide secretion together with HlyBD (and a functional to IC). Immunization and efficacy evaluations are performed as described above.

9.6. Example

Control of Bacterial Infection with Gluconate

As described herein, in an msbB⁻ zwf⁻ strains are sensitive to physiological concentrations of $CO_2$ in the presence of gluconate. The ability of gluconate to control excessive bacterial infections, such as might occur in a patient who becomes immunocompromised or otherwise has their health complicated such that the proliferation of the bacteria requires control, can be modeled using immunocompromised mice, such as nude (nu/nu) or severe combined immunodeficient (SCID) mice.

1) The msbB⁻ zwf⁻ *Salmonella* cultured on LB agar overnight at 37°.

2) The following day the bacteria are transferred to LB broth, adjusted in concentration to $OD_{600}$=0.1 (~$2\times10^8$ cfu/ml), and subjected to further growth at 37° on a rotator to $OD_{600}$=2.0, and placed on ice, where the concentration corresponds to approx. $4\times10^9$ cfu/ml.

3) Following growth, centrifuged and resuspended in 1/10 the original volume in a pharmacologically suitable buffer such as PBS and they are diluted to a concentration of $10^4$ to $10^9$ c.f.u./ml in a pharmacologically suitable buffer on ice, warmed to room temperature and administered orally or intranasally in a volume appropriate for the size of the animal in question, for example, not more than 10 µl/g body weight for a mouse. The actual dose measured in total cfu is determined by the safe dose as described by Bermudes (WO/2008/03908), depending upon the stain of bacteria.

4) A dose response of 1, 5, 50 or 100 mg/mouse (50 mg, 250 mg, 2.5 g, 5 g/kg) of gluconate is given either orally or by intravenous administration.

5) After 1 week, a blood or tissue sample is taken for comparison to the pretreatment sample using a colony forming unit assay.

6) Survival of the mice is monitored over time.

Other Embodiments

Other embodiments are within the claims set forth below. For example, the host bacterium can be *E. coli* or any other lipid mutant or non-lipid mutant enteric bacterium found to be sensitive to $CO_2$, acidic pH and/or osmolarity, including those of the genera *Salmonella, Bordetella, Shigella, Yersenia, Citrobacter, Enterobacter, Klebsiella, Morganella, Proteus, Providencia, Serratia, Plesiomonas*, and *Aeromonas*, all of which are known or believed to have cell wall structures similar to *E. coli* and *Salmonella*.

The various aspects of the disclosure may be combined and subcombined to represent all consistent combinations and subcombinations without departing from the scope of the invention. The invention is limited by neither the specific embodiments of the specification, nor the particular scope of the claims, but rather is to be treated as encompassing the full scope of each aspect disclosed, and the various combinations and permutations, which do not depart from the enabled disclosure herein.

What is claimed is:

1. A live attenuated stress-resistant *Salmonella* species (sp.) genetically engineered from a wild type *Salmonella* sp., the wild type *Salmonella* having an msbB gene and a zwf gene, and producing pyrogenic Lipid A, and comprising an intact pentose pathway,
 the mutant *Salmonella* sp. comprising:
  a defective msbB gene resulting in reduction of Lipid A pyrogenicity compared to the wild type *Salmonella*, and
  a defect in the zwf gene which interrupts the pentose phosphate pathway,
  the mutant *Salmonella* sp. growing under conditions of at least one of: (a) pH 6.7 in air, (b) 5% $CO_2$, and (c) 300 milliosmoles.

2. The mutant *Salmonella* sp. according to claim 1, wherein the mutant *Salmonella* sp. is inhibited or killed by the addition of gluconate at a level which does not kill or inhibit wild type *Salmonella*.

3. The mutant *Salmonella* sp. according to claim 1, which is further engineered to contain one or more nucleic acid molecules encoding one or more therapeutic agents.

4. The mutant *Salmonella* sp. according to claim 3, in combination with a pharmaceutically acceptable carrier.

5. The mutant *Salmonella* sp. according to claim 4, wherein the pharmaceutically acceptable carrier is formulated for oral administration to a human.

6. The mutant *Salmonella* sp. according to claim 3, wherein the mutant *Salmonella* sp. is adapted to colonize human gut, and produce a therapeutically effective amount of the one or more therapeutic agents within the human gut.

7. The mutant *Salmonella* sp. according to claim 3, wherein the one or more nucleic acid molecules encode a secreted antigen.

8. The mutant *Salmonella* sp. according to claim 3, wherein the one or more nucleic acid molecules encode an antigen heterologous to *Salmonella*.

9. The mutant *Salmonella* sp. according to claim 3, wherein the one or more nucleic acid molecules encode a viral antigen.

10. The mutant *Salmonella* sp. according to claim 3, wherein the one or more nucleic acid molecules encoding one or more therapeutic agents comprise one or more nucleic acid molecules encoding one or more therapeutic agents fused to a secretion promoter.

11. The mutant *Salmonella* sp. according to claim 3, wherein the one or more nucleic acid molecules encoding one or more therapeutic agents encode a non-bacterial protein, wherein the nucleic acid molecules are optimized for bacterial expression by use of bacterial codons.

12. A live attenuated stress-resistant *Salmonella* sp. genetically engineered from a wild type *Salmonella* sp., said mutant *Salmonella* having a defective msbB gene in the lipopolysaccharide biosynthetic pathway and resulting in reduced Lipid A pyrogenicity with respect to the respective wild type *Salmonella* having an intact lipopolysaccharide biosynthetic pathway comprising a non-defective msbB gene, and a defective zwf gene in the pentose phosphate pathway which reduces synthesis of pentose phosphate as compared to the wild type *Salmonella* having the intact lipopolysaccharide biosynthetic pathway comprising the non-defective msbB gene, the mutant *Salmonella* sp. exhibiting growth after at least 2 hours under incubation conditions selected from the group consisting of at least one of:
 a growth medium having a pH 6.7 in air;
 a growth medium subjected to 5% $CO_2$, and
 a growth medium having an osmolarity of 300 milliosmoles.

13. The mutant *Salmonella* sp. according to claim 12, further comprising a nucleic acid molecule encoding a therapeutic agent which is secreted from the mutant *Salmonella* sp.

14. A live attenuated stress-resistant *Salmonella* sp. genetically engineered from a wild type *Salmonella* sp. comprising an intact lipopolysaccharide biosynthetic pathway comprising a non-defective msbB gene, said mutant *Salmonella* comprising:
 an altered lipopolysaccharide pathway comprising a defective msbB gene, resulting in reduced Lipid A pyrogenicity with respect to the wild type *Salmonella*; and
 an altered pentose phosphate pathway comprising a defective zwf gene, which reduces synthesis of pentose,
 the mutant *Salmonella* sp. being characterized by exhibition of growth after at least 2 hours under incubation conditions selected from the group consisting of at least one of:
 a growth medium having a pH 6.7 in air;
 a growth medium subjected to 5% $CO_2$, and
 a growth medium having an osmolarity of 300 milliosmoles.

15. The mutant *Salmonella* sp. according to claim 14, further comprising a nucleic acid molecule encoding a therapeutic agent which is secreted from the mutant *Salmonella* sp.

16. The mutant *Salmonella* sp. according to claim 15, wherein the nucleic acid molecule encoding the therapeutic agent encodes a non-bacterial protein, wherein the nucleic acid molecule is optimized for bacterial expression by use of bacterial codons.

* * * * *